United States Patent [19]

Shiokawa et al.

[11] Patent Number: 5,256,824
[45] Date of Patent: Oct. 26, 1993

[54] SUBSTITUTED-AMINE COMPOUND AND A PROCESS FOR THE PREPARATION THEREOF

[75] Inventors: Youichi Shiokawa, Ibaraki; Kazuo Okumura, Osaka; Kazuhiko Take, Tondabayashi; Kazunori Tsubaki, Suita, all of Japan

[73] Assignee: Fujisawa Pharmaceutical Co., Ltd., Osaka, Japan

[21] Appl. No.: 665,669

[22] Filed: Mar. 7, 1991

[30] Foreign Application Priority Data

Mar. 8, 1990 [GB] United Kingdom ............... 9005247
Oct. 8, 1990 [GB] United Kingdom ............... 9021806

[51] Int. Cl.$^5$ ............................................. C07C 211/40
[52] U.S. Cl. ............................. 564/307; 544/107; 544/178; 544/403; 558/47; 564/1; 564/452
[58] Field of Search ...................... 564/307; 514/647

[56] References Cited

U.S. PATENT DOCUMENTS

| 3,285,960 | 11/1966 | Halverstadt | 564/307 |
| 3,376,312 | 4/1968 | Unger et al. | 548/578 |
| 3,455,944 | 7/1969 | Robison | 564/307 |
| 3,479,352 | 11/1969 | Alt | 544/106 |
| 4,141,993 | 2/1979 | Carnmalm et al. | 514/646 |

FOREIGN PATENT DOCUMENTS

| 273065 | 7/1969 | Austria . |
| 658248 | 1/1965 | Belgium . |
| 1793611 | 10/1971 | Fed. Rep. of Germany . |
| 2227844 | 1/1973 | Fed. Rep. of Germany . |

OTHER PUBLICATIONS

Acta Pharmaceutical Suecica vol. 12, 1975, Stockholm, pp. 149–172; B. Carnmalm et al.: "Antidepressant Agents".

*Primary Examiner*—Glennon H. Hollrah
*Assistant Examiner*—Scott C. Rand
*Attorney, Agent, or Firm*—Oblon, Spivak, McClelland, Maier & Neustadt

[57] ABSTRACT

The compound (−)-N-t-butyl-4,4-diphenyl-2-cyclopentenylamine, or its hydrochloride salt has anticholinergic activity, and thus has a variety of pharmaceutical utilities.

1 Claim, No Drawings

SUBSTITUTED-AMINE COMPOUND AND A PROCESS FOR THE PREPARATION THEREOF

This invention relates to a novel substituted-amine compound and a pharmaceutically acceptable salt thereof.

More particularly, it relates to a novel substituted-amine compound and a pharmaceutically acceptable salt thereof which have anticholinergic activity and sodium channel blocking activity, and are useful for the prevention and/or treatment of dysuria such as pollakiuria, urinary incontinence or the like in case of nervous pollakiuria, neurogenic bladder dysfunction, nocturia, unstable bladder, cystospasm, chronic cystitis, chronic prostatitis or the like; and for the prevention and/or treatment of spasm and/or hypanakinesis in case of gastric ulcer, duodenal ulcer, gastroxynsis, esophagospasm, gastritis, enteritis, irritable colon syndrome, enteralgia, cholecystitis, cholangitis, pylorospasm, pancreatitis, pain in case of pancreatitis, biliary dyskinesia, aftereffect after cholecystectomy, urinary calculus, cystitis, dysmenorrhea, hidrosis, spasm of urinary tract; and for the prevention and/or treatment of arrhythmia, congestive heart failure, or the like; and useful as local anesthetic; and which are expected to be useful for the prevention and/or treatment of asthma, Parkinson disease, angina pectris or the like; to a process for the preparation thereof, to a pharmaceutical composition comprising the same and to a method for the prevention and/or treatment of aforesaid diseases in human being or animals.

One object of this invention is to provide a novel substituted-amine compound and a pharmaceutically acceptable salt thereof which are useful for the prevention and/or treatment of aforesaid diseases.

Another object of this invention is to provide a process for the preparation of said substituted-amine compound or a salt thereof.

A further object of this invention is to provide a pharmaceutical composition comprising, as an active ingredient, said substituted-amine compound or a pharmaceutically acceptable salt thereof, which is useful as an agent for the prevention and/or treatment of aforesaid diseases.

Still further object of this invention is to provide a therapeutical method for the prevention and/or treatment of aforesaid diseases.

The object substituted-amine compound (I) of the present invention is shown by the following formula (I):

$$R^1, R^2 \text{---} A \text{---} N(R^3)(R^4) \text{ with } R^5, R^6 \quad (I)$$

wherein a group of the formula:

$$\text{(A)}$$

is cyclo(lower)alkyl or cyclo(lower)alkenyl, $R^1$ and $R^2$ are each hydrogen, lower alkyl, cyclo(lower)alkyl or aryl which may have one or more suitable substituent(s), $R^3$ is lower alkyl which may have one or more suitable substituent(s), lower alkynyl which may have one or more suitable substituent(s) or cyclo(lower)alkyl which may have one or more suitable substituent(s), $R^4$ is hydrogen, lower alkyl or ar(lower)alkyl, in which $R^3$ and $R^4$ may be linked together to form a heterocyclic group which may have one or more suitable substituent(s), $R^5$ and $R^6$ are each hydrogen or hydroxy, with proviso that (i) $R^3$ is t-butyl, when a group of the formula:

$$\text{(A)}$$

is cyclopentyl, $R^1$ and $R^2$ are each phenyl which may have chloro, and $R^5$ and $R^6$ are each hydrogen, (ii) $R^3$ is t-butyl, when a group of the formula:

$$\text{(A)}$$

is cyclohexyl, $R^1$ and $R^2$ are each phenyl, and $R^5$ is hydrogen, (iii) $R^3$ is t-butyl, when a group of the formula:

$$\text{(A)}$$

is cyclohexenyl, $R^1$ and $R^2$ are each phenyl, and $R^5$ and $R^6$ are each hydrogen, and (iv) $R^3$ is t-butyl, when a group of the formula:

$$\text{(A)}$$

is cyclopentenyl, and $R^1$, $R^2$, $R^5$ and $R^6$ are each hydrogen.

The object substituted-amine compound (I) of the present invention can be prepared by the processes as illustrated in the following reaction schemes.

Process 1

$$R^1,R^2\text{---}A(R^5,R^6)\text{---}X + H\text{---}N(R^3)(R^4) \longrightarrow R^1,R^2\text{---}A(R^5,R^6)\text{---}N(R^3)(R^4)$$

(II)    (III) or a salt thereof    (I) or a salt thereof

Process 2

-continued

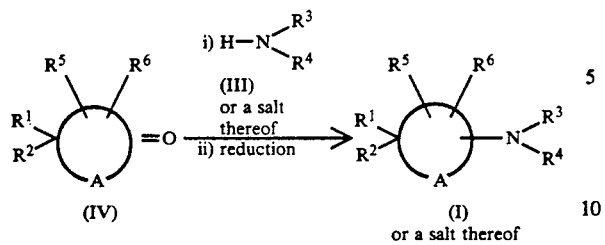

Process 3

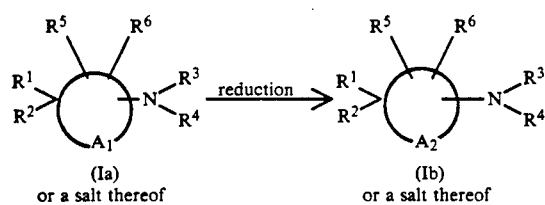

Process 4

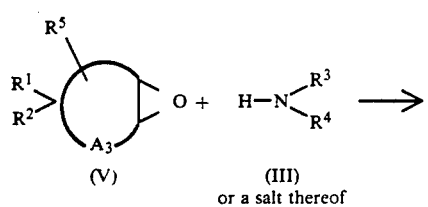

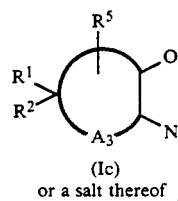

Process 5

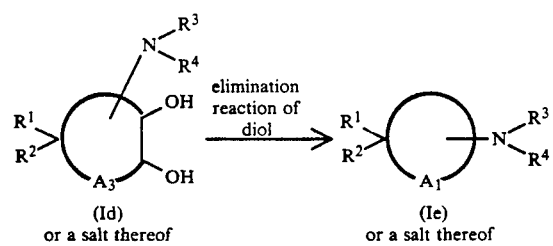

Process 6

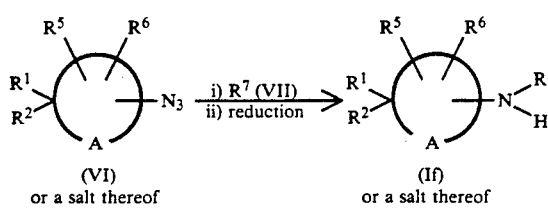

wherein a group of the formula:

$(A)$, $R^1$, $R^2$, $R^3$, $R^4$, $R^5$ and $R^6$ are each as defined above, a group of the formula:

$(A_1)$ is cyclo(lower)alkenyl,
a group of the formula:

$(A_2)$ is cyclo(lower)alkyl,
a group of the formula:

$(A_3)$ is cyclo(lower)alkyl or cyclo(lower)alkenyl,
a compound of the formula: $R^7$ is lower alkanone or lower alkanal, each of which may have one or more suitable substituent(s), lower alkynone or lower alkynal, each of which may have one or more suitable substituent(s), or cyclo(lower)alkanone which may have one or more suitable substituent(s), and X is a leaving group.

Among the starting compounds, some of the compounds (II) and (VI) are novel and can be prepared by the following reaction schemes.

Process A

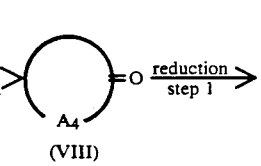

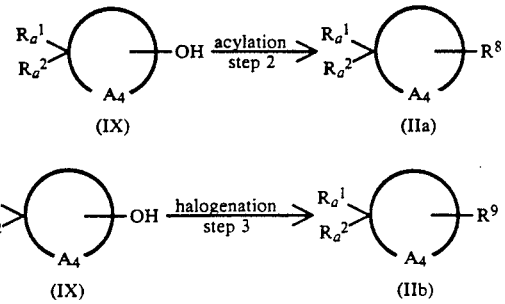

Process B $$\underset{(\text{IIc})}{\underset{R_a^2}{\overset{R_a^1}{\bigcirc}}\!\!\!\!-X} \xrightarrow[\text{azide group}]{\text{substitution reaction by}} \underset{(\text{VIa})\text{ or a salt thereof}}{\underset{R_a^2}{\overset{R_a^1}{\bigcirc}}\!\!\!\!-N_3}$$

wherein $R_a^1$ and $R_a^2$ are each lower alkyl, cyclo(lower)alkyl or aryl which may have one or more suitable substituent(s),
$R^8$ is acyloxy,
$R^9$ is halogen,
X is as defined above, a group of the formula:

$$\bigcirc_A$$

is as defined above, and a group of the formula:

$$\bigcirc_{A_4}$$

is cyclo(lower)alkyl or cyclopentenyl.

Some of the starting compounds (IV) and (V) are novel and can be prepared according to the methods disclosed in *Preparations* mentioned later in the present specification or the similar manners thereto.

As for the object substituted-amine compound (I), it is to be noted that the compound (I) can include the stereo isomers due to the asymmetric carbon atom(s).

Suitable pharmaceutically acceptable salts of the object compound (I) are conventional non-toxic mono or di salts and include an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, hydroiodide, sulfate, phosphate, etc.], a salt with an amino acid [e.g. arginine salt, aspartic acid salt, glutamic acid salt, etc.], and the like.

In the above and subsequent descriptions of this specification, suitable examples of the various definitions are explained in detail as follows:

The term "lower" is intended to mean 1 to 6 carbon atom(s), unless otherwise indicated.

Suitable "cyclo(lower)alkyl" may include cyclopropyl, cyclobutyl, cyclopentyl and cyclohexyl, and the like, in which the preferred one may be cyclo($C_3$-$C_6$)alkyl, and the more preferred one may be cyclopropyl, cyclobutyl, cyclopentyl and cyclohexyl.

Said "cyclo(lower)alkyl" may have one or more (preferably 1 to 3) suitable substituent(s) such as lower alkyl (e.g. methyl, ethyl, propyl, isopropyl, butyl, t-butyl, pentyl, hexyl, etc.) or the like.

Suitable "cyclo(lower)alkenyl" may include cyclopropenyl, cyclobutenyl, cyclopentenyl, 2,4-cyclopentadienyl, cyclohexenyl, 1,3-cyclohexadienyl, and the like, in which the preferred one may be cyclo($C_5$-$C_6$)alkenyl and the more preferred one may be cyclopentenyl and cyclohexenyl.

Suitable "lower alkyl" may include the straight or branched ones such as methyl, ethyl, propyl, isopropyl, butyl, t-butyl, pentyl, hexyl, or the like, in which the preferred one may be ($C_1$-$C_4$)alkyl and the more preferred one may be methyl, ethyl, isopropyl, butyl and t-butyl.

Said "lower alkyl" may have one or more (preferably 1 to 3) suitable substituent(s) such as hydroxy; aryl as explained below; N-(lower)-alkyl-N-ar(lower)alkylamino, in which suitable "lower alkyl" moiety can be referred to aforesaid "lower alkyl", and suitable "ar(lower)alkyl" moiety can be referred to the ones as exemplified below for "ar(lower)alkyl"; or the like; and the concrete examples of said "N-(lower)alkyl-N-ar(lower)alkylamino" may be N-methyl-N-benzylamino, N-ethyl-N-benzylamino, N-propyl-N-phenethylamino, or the like, in which the preferred one may be N-($C_1$-$C_4$)alkyl-N-phenyl($C_1$-$C_4$)alkylamino and the more preferred one may be N-methyl-N-benzylamino; or the like.

Suitable "lower alkynyl" may include straight or branched ones such as ethynyl, 2-propynyl, 1-propynyl, 2-butynyl, 2-methyl-3-butynyl, 3-pentynyl, 1,1-dimethyl-2-butynyl, 5-hexynyl, in which the preferred one may be ($C_2$-$C_6$)alkynyl, the more preferred one may be ($C_4$-$C_6$)alkynyl and the most preferred one may be 1,1-dimethyl-2-butynyl.

Said "lower alkynyl" may have one or more (preferably 1 to 3) suitable substituent(s) such as N,N-di(lower)alkylamino; in which suitable "lower alkyl" moiety can be referred to aforesaid "lower alkyl"; or the like; and the concrete examples of said N,N-di(lower)alkylamino may be N,N-dimethylamino, N-methyl-N-ethylamino, N,N-diethylamino, N,N-dipropylamino, N-isopropyl-N-butylamino, N,N-dipentylamino, N,N-dihexylamino, or the like, in which the preferred one may be N,N-di($C_1$-$C_4$)alkylamino and the more preferred one may be N,N-diethylamino.

Suitable "aryl" may include phenyl, naphthyl, pentalenyl, and the like, in which the preferred one may be phenyl.

Said "aryl" may have one or more (preferably 1 to 3) suitable substituent(s) such as aforesaid lower alkyl, or the like.

Suitable "ar(lower)alkyl" may include mono-(or di- or tri-)phenyl(lower)alkyl such as benzyl, phenethyl, benzhydryl, trityl or the like, and the like; in which the preferred one may be phenyl(lower)alkyl, the more preferred one may be phenyl($C_1$-$C_4$)alkyl, and the most preferred one may be benzyl.

Suitable "a heterocyclic group" in case $R^3$ and $R^4$ are linked together to form "a heterocyclic group" may be N-containing heterocyclic group.

Suitable "N-containing heterocyclic group" may include saturated or unsaturated, monocyclic or polycyclic heterocyclic group such as unsaturated 3 to 8-membered (more preferably 5 to 7-membered) heteromonocyclic group containing 1 to 4 nitrogen atom(s), for example, 1-azepinyl (e.g. 1H-azepin-1-yl, etc.) 1-pyrrolyl, 1-pyrrolinyl, 1-imidazolyl, 1-pyrazolyl, 1-pyridyl, 1-dihydropyridyl, 1-pyrimidinyl, 1-pyrazinyl, 1-pyridazinyl, triazolyl (e.g. 4H-1,2,4-triazol-4-yl, 1H-1,2,3-triazol-1-yl, 2H-1,2,3-triazol-2-yl, etc.), tetrazolyl (e.g. 1H-tetrazol-1-yl, 2H-tetrazol-2-yl, etc.) etc.;

saturated 3 to 8-membered (more preferably 5 to 7 membered) heteromonocyclic group containing 1 to 4 nitrogen atom(s), for example, perhydroazepin-1-yl (e.g. perhydro-1H-azepin-1-yl, etc.) 1-pyrrolidinyl, 1-imidazolidinyl, piperidino, 1-piperazinyl, etc.;

unsaturated condensed heterocyclic group containing 1 to 4 nitrogen atom(s), for example, 1H-indol-1-yl, 2-isoindolyl, 1H-benzimidazol-1-yl, 1H-indazol-1-yl, 2H-benzotriazol-2-yl, etc.;

saturated condensed heterocyclic group containing 1 to 4 nitrogen atom(s), for example, 7-azabicyclo[2.2.1]heptan-7-yl, 3-azabicyclo[3.2.2]nonan-3-yl, etc.]

unsaturated 3 to 8-membered (more preferably 5 or 6-membered) heteromonocyclic group containing 1 to 2 oxygen atom(s) and 1 to 3 nitrogen atom(s), for example, 2,3-dihydroxazol-3-yl, etc.;

saturated 3 to 8-membered (more preferably 5 or 6-membered) heteromonocyclic group containing 1 to 2 oxygen atom(s) and 1 to 3 nitrogen atom(s), for example, morpholino, 3-perhydroxazolyl, etc.;

unsaturated condensed heterocyclic group containing 1 to 2 oxygen atom(s) and 1 to 3 nitrogen atom(s), for example, 2,3-dihydrobenzoxazol-3-yl, etc.;

unsaturated 3 to 8-membered (more preferably 5 or 6-membered)heteromonocyclic group containing 1 to 2 sulfur atom(s) and 1 to 3 nitrogen atom(s), for example, 2,3-dihydrothiazol-3-yl, etc.;

saturated 3 to 8-membered (more preferably 5 or 6-membered) heteromonocyclic group containing 1 to 2 sulfur atom(s) and 1 to 3 nitrogen atom(s), for example, 1,3-thiazolidin-3-yl, etc.;

unsaturated condensed heterocyclic group containing 1 to 2 sulfur atom(s) and 1 to 3 nitrogen atom(s), for example, 2,3-dihydrobenzothiazol-3-yl, etc.; in which the preferred one may be saturated 3 to 8- membered heteromonocyclic group containing 1 to 4 nitrogen atom(s) and saturated 3 to 8- membered heteromonocyclic group containing 1 to 2 oxygen atom(s) and 1 to 3 nitrogen atom(s), and the more preferred one may be 1-piperazinyl and morpholino.

Said "a heterocyclic group" may have one or more (preferably 1 to 3) suitable substituent(s) such as lower alkanoyl (e.g. formyl, acetyl, propionyl, butyryl, pentanoyl, hexanoyl, etc.) or the like.

Suitable "lower alkanone" may include acetone, 2-butanone, 3-methyl-2-butanone, 3-pentanone, 2-hexanone, and the like, in which the preferred one may be ($C_3$–$C_4$)alkanone and the more preferred one may be acetone.

Suitable "lower alkanal" may include formaldehyde, ethanal, propanal, butanal, 2-methylpropanal, pentanal, hexanal and the like, in which the preferred one may be ($C_1$–$C_4$)alkanal.

Said "lower alkanone" and "lower alkanal" may have one or more (preferably 1 to 3) suitable substituent(s) such as hydroxy, aforesaid aryl, aforesaid N-(lower)alkyl-N-ar(lower)alkylamino or the like.

Suitable "lower alkynone" may include 3-butyn-2-one, 3-pentyn-2-one, 3-methyl-4-pentyn-2-one, 5-hexyn-3-one and the like, in which the preferred one may be ($C_4$–$C_6$)alkynone.

Suitable "lower alkynal" may include propynal, 2-butynal, 4-pentynal, 2-methyl-3-butynal, 4-hexynal and the like, in which the preferred one may be ($C_4$–$C_6$)alkynal.

Said "lower alkynone" and "lower alkynal" may have one or more (preferably 1 to 3) suitable substituent(s) such as aforesaid N,N-di(lower)alkylamino, or the like.

Suitable "cyclo(lower)alkanone" may include cyclopropanone, cyclobutanone, cyclopentanone, cyclohexanone and the like, in which the preferred one may be cyclo($C_3$–$C_6$)alkanone.

Said "cyclo(lower)alkanone" may have one or more (preferably 1 to 3) suitable substituent(s) such as aforesaid lower alkyl or the like.

Suitable "a leaving group" may include halogen (e.g. chloro, fluoro, bromo, iodo); acyloxy such as lower alkanoyloxy (e.g. acetoxy, propionyloxy, butyryloxy, pentanoyloxy, hexanoyloxy, etc.) sulfonyloxy (e.g. mesyloxy, ethylsulfonyloxy, tosyloxy, etc.) or the like; and the like.

In the object substituted-amine compound (I), one of very preferred compound can be shown by the following formula (I-1):

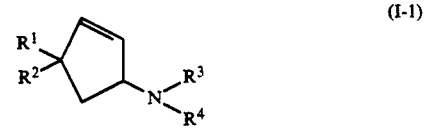

wherein $R^1$, $R^2$, $R^3$ and $R^4$ are each as defined above, in which the preferred $R^1$ and $R^2$ may be each aryl which may have one or more suitable substituent(s), the more preferred ones may be each phenyl which may have 1 to 3 lower alkyl, and the most preferred ones may be each phenyl; the preferred $R^3$ may be lower alkyl which may have one or more suitable substituent(s), the more preferred one may be lower alkyl and the most preferred one may be t-butyl; and the preferred $R^4$ may be hydrogen and lower alkyl and the more preferred one may be hydrogen.

Another very preferred compound among the object substituted-amine compound (I) can be shown by the following formula (I-2):

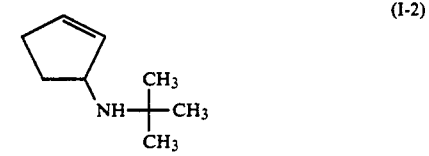

The other very preferred compound among the object substituted-amine compound (I) can be shown by the following formula (I-3):

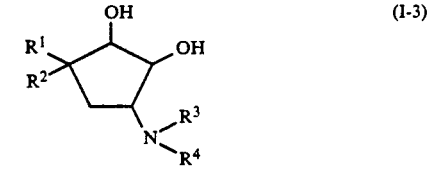

wherein $R^1$, $R^2$, $R^3$ and $R^4$ are each as defined above, in which the preferred $R^1$ and $R^2$ may be each aryl which may have one or more suitable substituent(s), the more preferred one may be phenyl which may have 1 to 3 lower alkyl and the most preferred one may be phenyl; the preferred $R^3$ may be lower alkyl which may have one or more suitable substituent(s), the more preferred one may be lower alkyl and the most preferred one may be ethyl, isopropyl and t-butyl; and the preferred $R^4$ may be hydrogen and lower alkyl and the more preferred one may be hydrogen and ethyl.

As to the foregoing, it is to be noted that in the above some very preferred compounds of the object substituted-amine compound (I) are only exemplified, and so the scope of the object substituted-amine compound (I) of the present invention is never limited at all to said very preferred ones exemplified above.

The processes for preparing the object compound (I) of the present invention are explained in detail in the following.

Process 1

The object compound (I) or a salt thereof can be prepared by reacting the compound (II) with the compound (III) or a salt thereof.

Suitable salt of the compound (III) can be referred to the ones as exemplified for the compound (I).

The present reaction may be carried out in a solvent such as water, phosphate buffer, acetone, chloroform, acetonitrile, nitrobenzene, methylene chloride, ethylene chloride, formamide, N,N-dimethylformamide, methanol, ethanol, diethyl ether, tetrahydrofuran, dimethyl sulfoxide, or any other organic solvent which does not adversely affect the reaction, preferably in ones having strong polarities. Among the solvents, hydrophilic solvents may be used in a mixture with water.

The reaction is preferably conducted in the presence of a base, for example, inorganic base such as alkali metal hydroxide, alkali metal carbonate, alkali metal bicarbonate, organic base such as trialkylamine, and the like.

The reaction temperature is not critical, and the reaction is usually carried out at room temperature, under warming or under heating.

The present reaction is preferably carried out in the presence of alkali metal halide [e.g. sodium iodide, potassium iodide, etc.], alkali metal thiocyanate [e.g. sodium thiocyanate, potassium thiocyanate, etc.] or the like.

In this reaction, the compound (II) may be converted from the corresponding alcohol compound by the conventional method (e.g. reaction with methanesulfonyl chloride, etc.) during the reaction.

As for this process, the following is to be noted.

When the group of the formula:

of the compound (II) is cyclo(lower)alkenyl, and the leaving group X is located at the allyl position of the double bond as illustrated by the following formula:

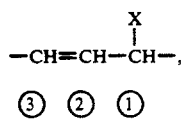

there may be the case the compound (III) reacts at position ③ instead of position ①, and this case is also included within the scope of the present invention.

Process 2

The object compound (I) or a salt thereof can be prepared by reacting the compound (IV) with the compound (III) or a salt thereof and then subjecting the resultant intermediate compound to reduction.

This reaction can be carried out without isolation of the intermediate compound.

i) The reaction of the compound (IV) with the compound (III) or a salt thereof is usually carried out in a conventional solvent such as alcohol (e.g. methanol, ethanol), methylene chloride, chloroform, or any other solvent which does not adversely influence the reaction.

The reaction temperature is not critical and the reaction can be carried out under cooling, at room temperature, under warming to heating.

ii) The reduction can be carried out by the reaction with a reducing agent, for example, metal hydride compound such as alkali metal aluminum hydride (e.g. lithium aluminum hydride, etc.), di(lower)alkylaluminum hydride (e.g. diisobutylaluminum hydride, etc.), alkali metal borohydride (e.g. sodium borohydride, etc.), or the like.

The reaction is usually carried out in a solvent such as diethyl ether, chloroform, methylene chloride, tetrahydrofuran, benzene, toluene, alcohol (e.g. methanol, ethanol, etc.) or any other solvent which does not adversely influence the reaction.

The reaction temperature is not critical and the reaction can be carried out under cooling, at room temperature or under warming.

When the group of the formula:

of the compound (IV) is cyclo(lower)alkenyl, there may be the case the double bond of said cyclo(lower)alkenyl group is also reduced to form the single bond during the reduction, and this case is also included within the scope of the present invention.

Process 3

The object compound (Ib) or a salt thereof can be prepared by subjecting the compound (Ia) or a salt thereof to reduction.

Suitable salts of the compounds (Ia) and (Ib) can be referred to the ones as exemplified for the compound (I).

The reduction method may include catalytic reduction, and the like.

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, ethyl acetate, diethyl ether, dioxane, tetrahydrofuran, or a mixture thereof.

The reaction temperature of this reduction is not critical and the reaction is usually carried out under cooling to warming.

Process 4

The object compound (Ic) or a salt thereof can be prepared by reacting the compound (V) with the compound (III) or a salt thereof.

The suitable salts of the compound (Ic) can be referred to the ones as exemplified for the compound (I).

The reaction of this step can be carried out according to a similar manner to that as explained in Process 1.

Process 5

The object compound (Ie) or a salt thereof can be prepared by subjecting the compound (Id) or a salt thereof to elimination reaction of diol.

The suitable salts of the compounds (Id) and (Ie) can be referred to the ones as exemplified for the compound (I).

The elimination reaction of this process can be carried out by reacting the compound (Id) or a salt thereof with aldehyde compound (e.g. benzaldehyde, etc.), tri(lower)alkyl orthoformate (e.g. trimethyl orthoformate, etc.), and then a base such as lower alkyl lithium (e.g. methyl lithium, n-butyl lithium, etc.) lithium di(lower)alkylamide (e.g. lithium diisopropylamide, etc.), alkali metal hydroxide (e.g. sodium hydroxide, etc.), or the like; or an acid such as lower alkanoic acid (e.g. acetic acid, propionic acid, etc.), sulfonic acid (e.g. p-toluenesulfonic acid, etc.).

This reaction is usually carried out in a solvent such as n-hexane, diethyl ether, tetrahydrofuran, methylene chloride, toluene, xylene, or any other solvent which does not adversely influence the reaction.

The reaction temperature is not critical and the reaction can be carried out at room temperature, under warming to heating.

Process 6

The object compound (If) or a salt thereof can be prepared by reacting the compound (VI) or a salt thereof with phosphine compound and the compound (VII), and then subjecting the resultant intermediate compound to reduction.

Suitable salts of the compounds (If) and (VI) can be referred to the ones as exemplified for the compound (I).

Suitable "phosphine compound" may include triphenylphosphine, and the like.

i) The reaction of the compound (VI) or a salt thereof with phosphine compound and the compound (VII) is usually carried out in a solvent such as diethyl ether, tetrahydrofuran, or any other solvent which does not adversely influence the reaction. When the compound (VII) is a liquid, it is also used as a solvent.

The reaction temperature is not critical and the reaction can be carried out at room temperature, under warming to heating.

ii) The reduction of this process can be carried out according to a similar manner to that as explained in Process 2.

The processes for the preparation of some of the starting compounds (II) and (VI) are explained in detail as follows.

PROCESS A

Step 1

The compound (IX) can be prepared by subjecting the compound (VIII) to reduction.

The reduction of this step can be carried out according to a similar manner to that as explained in Process 2.

Step 2

The compound (IIa) can be prepared by subjecting the compound (IX) to acylation.

The acylation of this step can be carried out by reacting the compound (IX) with an acid corresponding to acyl group to be introduced or its reactive derivative or a salt thereof.

The reaction can be carried out in a conventional manner in this field of the art, for example, by the method disclosed in Preparation of the present specification.

Step 3

The compound (IIb) can be prepared by subjecting the compound (IX) to halogenation.

The halogenation of this step can be carried out by reacting the compound (IX) with carbon tetrahalide (e.g. carbon tetrachloride, carbon tetrabromide, etc.), thionyl halide (e.g. thionyl chloride, etc.) or the like.

The reaction can be carried out in a conventional manner in this field of the art, for example, by the method disclosed in Preparation of the present specification.

PROCESS B

The compound (VIa) or a salt thereof can be prepared by subjecting the compound (IIc) to substitution reaction by azide group.

The substitution reaction of this process can be carried out by reacting the compound (IIc) with an azide compound such as alkali metal azide (e.g. sodium azide, etc.) or the like.

The reaction can be carried out in a conventional manner in this field of the art, for example, by the method disclosed in Preparation of the present specification.

The object compound (I) and a pharmaceutically acceptable salt thereof of this invention have anticholinergic activity and sodium channel blocking activity and are useful for the treatment of dysuria or other diseases a mentioned before in human being and animals.

In the object compound (I) and a pharmaceutically acceptable salt thereof, side effect such as mydriasis or the like is alleviated.

In order to illustrate the usefulness of the object compound (I) and a pharmaceutically acceptable salt thereof, the pharmacological test data of the representative compound of this invention are shown in the following.

Test on Inhibition of Urinary Bladder Contractions Induced by Water Filling in Rats

[I] Test Method

Male Sprague-Dawly rats, weighing 240–450 g, were anesthetized with urethane 1.0 g/kg s.c. The bladder was exposed through a midline incision in the abdomen for the recording of pressure within the bladder as follows; a balloon attached to one end of a stainless steel tube (O.D., 1.2 mm, 5 cm in length) was inserted into the bladder through a small incision in the bladder dome. The other end of the tube was connected to a pressure-transducer. The ureters were ligated and cut, and the proximal cut end was cannulated with polyethylene tubing and the urine was led outside.

Hyperactive urinary bladder (hyperactive contractions of the detrusor muscle) was induced by water filling of the bladder. Therefore, the balloon in the bladder was filled with water of a volume which caused a resting pressure of about 10 mmHg. Systemic blood pressure and heart rate were monitored from the common carotid artery.

When the contractile responses to water filling became constant, test compounds were administered intravenously.

[II] Test Compound
(−)-N-t-Butyl-4,4-diphenyl-2-cyclopentenylamine methanesulfonate
[III] Test Result
$ED_{30}=0.18$ (mg/kg)

Test on Na channel blocking activity

[I] Test Method
Male Japanese white rabbits weighing 2.0–3.0 kg were to evaluate the local anesthetic effect of test compound on the corneal blink reflex. Corneal reflexes were elicited by pressing a flexible monofilament (rabbit whisker) against the cornea. 1.0% Test compound solution in saline was applied to one eye (50 μl drops) and the contralateral eye received as a control. Corneal blink responses were scored at 5, and 15 minutes after test compound application.

Local anesthetic activities were expressed as an inhibition percent of blink responses.

[II] Test Compound
(−)-N-t-Butyl-4,4-diphenyl-2-cyclopentenylamine hydrochloride
[III] Test Result

|            | Inhibition % |
|------------|--------------|
| 5 minutes  | 100          |
| 15 minutes | 100          |

The pharmaceutical composition of this invention can be used in the form of a pharmaceutical preparation, for example, in solid, semisolid or liquid form, which contains the object compound (I) or a pharmaceutically acceptable salt thereof, as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation or intravesica administration. The active ingredient may be compounded, for example, with the usual non-toxic, pharmaceutically acceptable carrier for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used. The object compound (I) or a pharmaceutical acceptable salt thereof is/are included in the pharmaceutical composition in an amount sufficient to produce the desired effect upon the process or condition of diseases.

For applying the composition to human being or animal, it is preferable to apply it by intravenous, intramuscular, pulmonary, or oral administration, or insufflation. While the dosage of therapeutically effective amount of the object compound (I) varies from and also depends upon the age and condition of each individual patient to be treated, in the case of intravenous administration, a daily dose of 0.01–20 mg of the object compound (I) per kg weight of human being or animal, in the case of intramuscular administration, a daily dose of 0.1–20 mg of the object compound (I) per kg weight of human being or animal, in case of oral administration, a daily dose of 0.5–50 mg of the object compound (I) per kg weight of human being or animal is generally given for treating or preventing the aforesaid diseases.

The following Preparations and Examples are given for the purpose of illustrating this invention in more detail.

Preparation 1

To a solution of 5,5-diphenyl-2-cyclopenten-1-one (1.0 g) and cerium trichloride 7 hydrate (1.59 g) in methanol (10 ml) and methylene chloride (4 ml) was added dropwise a solution of sodium borohydride (0.16 g) in ethanol (6 ml) at 0° C. to 3° C. To the reaction mixture, cerium trichloride 7 hydrate (0.80 g) and sodium borohydride (0.08 g) were added 4 times an hour. After the reaction finished, cold water (30 ml) was added, and the mixture was extracted with chloroform. The extract was washed with brine, dried over magnesium sulfate and evaporated in vacuo. The residue was purified by column chromatography on silica gel with methylene chloride as an eluent to give 5,5-diphenyl-2-cyclopenten-1-ol 0.83 g).

IR (Neat): 3550, 3420 cm$^{-1}$
NMR (CDCl$_3$, δ): 1.28 (1H, broad s), 2.82–3.00 (1H, m), 3.40–3.55 (1H, m), 5.45 (1H, s), 5.88–5.98 (1H, m), 6.08–6.20 (1H, m), 7.10–7.40 (10H, m)

EXAMPLE 1

To a solution of 5,5-diphenyl-2-cyclopenten-1-ol (0.20 g) in N,N-dimethylformamide (1 ml) were added methanesulfonyl chloride (0.35 ml) and triethylamine (0.60 ml) at 5° to 10° C. After being stirred for 1 hour, t-butylamine (1.78 ml) was added to the reaction mixture at 5° to 12° C. The reaction mixture was stirred for 3 days at room temperature. To the reaction mixture were added water and ethyl acetate. The organic layer was separated, washed with water, dried over magnesium sulfate and evaporated in vacuo. The residue was purified by column chromatography on silica gel with a mixture of chloroform and methanol as an eluent to give N-t-butyl-4,4-diphenyl-2-cyclopentenylamine (0.11 g).

NMR (CDCl$_3$, δ): 0.80–1.40 (1H, broad m), 1.12 (9H, s), 2.04 (1H, dd, J=7.6 Hz and 13.0 Hz), 3.09 (1H, dd, J=6.8 Hz and 13.0 Hz), 3.94–4.10 (1H, m), 5.85 (1H, dd, J=1.7 Hz and 5.6 Hz), 6.21 (1H, dd, J=2.0 Hz and 5.6 Hz), 7.09–7.38 (10H, m)

EXAMPLE 2

N-t-Butyl-4,4-diphenyl-2-cyclopentenylamine methanesulfonate was obtained according to a conventional manner from the corresponding free amine compound of Example 1.

mp. 204°–206° C.
IR (Nujol): 1600, 1490 cm$^{-1}$
NMR (DMSO-d$_6$, δ): 1.42 (9H, s), 2.50 (3H, s), 2.79 (1H, dd, J=13.1 Hz and 8.9 Hz), 3.23 (1H, dd, J=13.1 Hz and 6.7 Hz), 4.18–4.34 (1H, m), 6.22 (1H, dd, J=5.7

Hz and 1.2 Hz), 6.36 (1H, dd, J=5.7 Hz and 2.1 Hz), 7.08-7.35 (10H, m), 8.67 (2H, broad s)

EXAMPLE 3

A mixture of (±)-N-t-butyl-4,4-diphenyl-2-cyclopentenylamine (17.22 g) and (−)-di-p-toluoyl-L-tartaric acid (11.69 g) in ethanol (30 ml) was refluxed and the resulting solution was allowed to stand at room temperature. After kept standing for 8 hours, the resulting precipitates were collected and recrystallized repeatedly with ethanol to give (+)-N-t-butyl-4,4-diphenyl-2-cyclopentenylamine.½[(−)-di-p-toluoyl-L-tartrate] (4.15 g). The resultant salt was added to 10% aqueous solution of sodium hydroxide and extracted with diethyl ether. The extract was washed with brine, dried over magnesium sulfate and evaporated in vacuo. The residue was purified by column chromatography on silica gel with a mixture of chloroform and methanol (20:1) as an eluent to give (+)-N-t-butyl-4,4-diphenyl-2-cyclopentenylamine (1.58 g).

$[\alpha]_D^{30} = +172.24$ (C=1.39, MeOH)

IR (Film): 3310, 3050, 1595 cm$^{-1}$

NMR (CDCl$_3$, δ): 0.60-1.60 (1H, broad m), 1.13 (9H, s), 2.04 (1H, dd, J=13.0 Hz and 7.7 Hz), 3.09 (1H, dd, J=13.0 Hz and 6.8 Hz), 4.04 (1H, dddd, J=7.7 Hz, 6.8 Hz, 2.0 Hz and 1.7 Hz), 5.86 (1H, dd, J=5.5 Hz and 1.7 Hz), 6.21 (1H, dd, J=5.5 Hz and 2.0 Hz), 7.09-7.47 (10H, m)

EXAMPLE 4

The previously obtained mother liquor of (+)-N-t-butyl-4,4-diphenyl-2-cyclopentenylamine.½[(−)-di-p-toluoyl-L-tartrate] was converted to the corresponding amine (9.44 g) by treatment of aqueous solution of sodium hydroxide. To the amine thus obtained (9.44 g) were added (+)-di-p-toluoyl-D-tartaric acid (6.50 g) and ethanol (25 ml) and the mixture was heated under reflux until a clear solution was obtained. After being allowed to stand at room temperature overnight, the resulting precipitates were collected by filtration and recrystallized repeatedly with ethanol to give (−)-N-t-butyl-4,4-diphenyl-2-cyclopentenylamine.½[(+)-di-p-toluoyl-D-tartrate] (6.90 g).

IR (Nujol): 1720, 1635 cm$^{-1}$

NMR (DMSO-d$_6$, δ): 1.18 (18H, s), 2.24 (2H, dd, J=13.2 Hz and 8.4 Hz), 2.35 (6H, s), 3.19 (2H, dd, J=13.2 Hz and 6.9 Hz), 4.18 (2H, broad t, J=7.4 Hz), 5.58 (2H, s), 5.92 (2H, d, J=5.5 Hz), 6.37 (2H, d, J=5.5 Hz), 7.07-7.38 (24H, m), 7.84 (4H, d, J=8.1 Hz)

EXAMPLE 5

(−)-N-t-Butyl-4,4-diphenyl-2-cyclopentenylamine.½-di-p-toluoyl-D-tartrate] (6.36 g) was added to 10% aqueous solution of sodium hydroxide and extracted with diethyl ether. The extract was washed with brine, dried over magnesium sulfate and evaporated in vacuo to give (−)-N-t-butyl-4,4-diphenyl-2-cyclopentenylamine (3.54 g).

IR (Film): 3310, 3050, 1595 cm$^{-1}$

NMR (CDCl$_3$, δ): 0.60-1.60 (1H, broad m), 1.13 (9H, s), 2.04 (1H, dd, J=13.0 Hz and 7.7 Hz), 3.09 (1H, dd, J=13.0 Hz and 6.8 Hz), 4.03 (1H, dddd, J=7.7 Hz, 6.8 Hz, 2.0 Hz and 1.7 Hz), 5.85 (1H, dd, J=5.5 Hz and 1.7 Hz), 6.21 (1H, dd, J=5.5 Hz and 2.0 Hz), 7.09-7.47 (10H, m)

EXAMPLE 6

To a solution of (−)-N-t-butyl-4,4-diphenyl-2-cyclopentenylamine (3.54 g) in ethyl acetate (20 ml) was added a solution of methanesulfonic acid (1.16 g) in ethyl acetate (1 ml). The solvent was evaporated in vacuo and diethyl ether was added. After kept standing for 4 hours, the resulting precipitate was collected by filtration to give (−)-N-t-butyl-4,4-diphenyl-2-cyclopentenylamine methanesulfonate (3.90 g).

$[\alpha]_D^{28} = -155.64°$ (C=1.05, MeOH)

mp: 150°-151° C.

IR (Nujol): 3400, 1600 cm$^{-1}$

NMR (CDCl$_3$, δ): 1.43 (9H, s), 2.51 (3H, s), 2.79 (1H, dd, J=13.1 Hz and 8.9 Hz), 3.24 (1H, dd, J=13.1 Hz and 6.7 Hz), 4.28 (1H, broad t, J=8.1 Hz), 6.22 (1H, d, J=5.7 Hz), 6.36 (1H, dd, J=5.7 Hz and 2.1 Hz), 7.08-7.35 (10H, m), 8.31-8.87 (2H, broad m)

EXAMPLE 7

(+)-N-t-Butyl-4,4-diphenyl-2-cyclopentenylamine methanesulfonate was obtained according to a similar manner to that of Example 6.

$[\alpha]_D^{29} = +155.84°$ (C=0.817, MeOH)

mp: 153°-154° C.

IR (Nujol): 3400, 1600 cm$^{-1}$

NMR (CDCl$_3$, δ): 1.42 (9H, s), 2.51 (3H, s), 2.79 (1H, dd, J=13.1 Hz and 8.9 Hz), 3.24 (1H, dd, J=13.1 Hz and 6.7 Hz), 4.28 (1H, broad t, J=8.1 Hz), 6.22 (1H, d, J=5.7 Hz), 6.37 (1H, dd, J=5.7 Hz and 2.0 Hz), 7.08-7.35 (10H, m), 8.08-9.27 (2H, broad m)

EXAMPLE 8

To a suspension of (−)-N-t-butyl-4,4-diphenyl-2-cyclopentenylamine methanesulfonate (0.70 g) in ethyl acetate was added 2N sodium hydroxide aqueous solution (10 ml), and the organic layer was separated. The solution was washed with brine and hydrogenated over 10% palladium-on-carbon (0.06 g) to give (−)-N-t-butyl-3,3-diphenylcyclopentylamine (0.53 g). To a solution of (−)-N-t-butyl-3,3-diphenylcyclopentylamine (0.53 g) in chloroform was added a solution of methanesulfonic acid (174 mg) in methanol. The solvent was evaporated in vacuo and triturated with diethyl ether to give (−)-N-t-butyl-3,3-diphenylcyclopentylamine methanesulfonate (0.63 g).

$[\alpha]_D^{23} = -4.75°$ (C=0.40,CH$_3$OH)

mp: 178° C.

NMR (CDCl$_3$, δ): 1.37 (9H, s), 2.00-2.70 (5H, m), 2.65 (3H, s), 3.10-3.28 (1H, m), 3.38-3.58 (1H, m), 7.05-7.30 (10H, m), 8.43 (2H, broad s)

EXAMPLE 9

(+)-N-t-Butyl-3,3-diphenylcyclopentylamine methanesulfonate was obtained according to a similar manner to that of Example 8.

$[\alpha]_D^{23} = +4.60°$ (C=1.0, MeOH)

mp: 178° C.

NMR (CDCl$_3$, δ): 1.37 (9H, s), 2.00-2.70 (5H, m), 2.65 (3H, s), 3.10-3.28 (1H, m), 3.38-3.58 (1H, m), 7.05-7.30 (10H, m), 8.43 (2H, broad s)

EXAMPLE 10

To a solution of (−)-N-t-butyl-4,4-diphenyl-2-cyclopentenylamine (8.82 g) in diethyl ether (50 ml) was added water (15 ml) and conc. hydrochloric acid (5 ml) at 0°-10° C. and stirred for 30 minutes. The resulting precipitate was collected by filtration and washed with diethyl ether to give (−)-N-t-butyl-4,4-diphenyl-2-cyclopentenylamine hydrochloride (9.70 g).

$[\alpha]_D^{26} = -189.4°$ (C=1.073, CH$_3$OH)

mp: 259°-261° C. (dec.)

IR (Nujol): 2730, 2690, 2640, 2610, 2475, 2440 cm$^{-1}$

NMR (CDCl$_3$, δ): 1.47 (9H, s), 3.10 (1H, dd, J=8.5 and 13.1 Hz), 3.17 (1H, dd, J=7.4 and 13.1 Hz), 4.23 (1H, broad s), 6.16 (1H, dd, J=5.7 and 2.3 Hz), 6.41 (1H, dd, J=5.7 and 1.4 Hz), 7.04–7.41 (10H, m), 9.64 (1H, broad s), 9.75 (1H, broad s)

Preparation 2

To a suspension of 5,5-diphenyl-2-cyclopenten-1-one (5.0 g) in toluene (25 ml) was added dropwise diisobutylaluminum hydride (15 ml, 1.5M solution in toluene) for 10 minutes at −78° C. to −50° C. After 30 minutes, ethyl acetate (5 ml) was added to the resultant yellow solution. The solution was acidified to pH 1 with 6N hydrochloric acid (20 ml) and extracted with ethyl acetate. The extract was washed with brine, dried over magnesium sulfate and evaporated in vacuo. The residue was purified by column chromatography on silica gel with methylene chloride as an eluent and further purified by bulb to bulb distillation to give 5,5-diphenyl-2-cyclopenten-1-ol (2.46 g).

bp: 200° C./0.4 mmHg

The physical data of this compound were identified with those of the compound of Preparation 1.

Preparation 3

To a solution of 5,5-diphenyl-2-cyclopenten-1-ol (0.70 g) in pyridine (5 ml) were added acetic anhydride (0.84 ml) and catalytic amount of 4-dimethylaminopyridine at room temperature. After being stirred for 30 minutes, the pH of the reaction mixture was adjusted to 1.0 with diluted hydrochloric acid and extracted with ethyl acetate. The extract was washed with brine, dried over magnesium sulfate and evaporated in vacuo to give 5,5-diphenyl-2-cyclopentenyl acetate (0.82 g).

IR (Neat): 1720 cm$^{-1}$

NMR (CDCl$_3$, δ): 1.68 (3H, s), 2.80–3.00 (1H, m), 3.48–3.70 (1H, m), 6.00–6.10 (1H, m), 6.14–6.26 (1H, m), 6.49 (1H, s), 7.10–7.35 (10H, m)

Preparation 4

To a mixture of 5,5-diphenyl-2-cyclopentenyl acetate (0.30 g) and sodium azide (84 mg) in a solution of tetrahydrofuran (3 ml) and water (1.5 ml) was added tetrakis(triphenylphosphine)palladium(O) (62 mg) at room temperature under an argon atmosphere. After being stirred for 14.5 hours, ethyl acetate was added. The organic layer was separated, washed with brine, dried over magnesium sulfate and evaporated in vacuo. The residue was purified by column chromatography on silica gel with a mixture of n-hexane and ethyl acetate as an eluent to give 4,4-diphenyl-2-cyclopentenyl azide (0.16 g).

IR (Neat): 2100 cm$^{-1}$

NMR (CDCl$_3$, δ): 2.45 (1H, dd, J=6 Hz and 14 Hz), 3.05 (1H, dd, J=14 Hz and 8 Hz), 4.42–4.70 (1H, m), 5.90 (1H, dd, J=2 Hz and 6 Hz), 6.42 (1H, dd, J=1 Hz and 6 Hz), 6.95–7.30 (10H, m)

Preparation 5

To a mixture of 2,2-diphenylacetonitrile (135.77 g), 2-propynyl chloride (52.35 g) and tetrabutylammonium hydrogen sulfate (0.51 g) was added dropwise 50% aqueous solution of sodium hydroxide (100 ml) at room temperature. After being stirred for 6 hours, the mixture was poured into water and extracted with diethyl ether. The extract was washed successively with diluted hydrochloric acid and brine, and evaporated in vacuo.

The residue was distilled in vacuo to give 2,2-diphenyl-2-(2-propynyl)acetonitrile.

bp: 138°–142° C. (0.3 mmHg)

IR (Film): 3290, 3060, 2240, 1600 cm$^{-1}$

NMR (CDCl$_3$, δ): 2.13 (1H, t, J=2.6 Hz), 3.25 (2H, d, J=2.6 Hz), 7.22–7.53 (10H, m)

Preparation 6

A mixture of 2,2-diphenyl-2-(2-propynyl)acetonitrile (1.38 g) and lithium aluminum hydride (0.21 g) in tetrahydrofuran (15 ml) was refluxed for 2 hours. The reaction mixture was poured into cold water, acidified with hydrochloric acid and extracted with diethyl ether. The extract was washed with brine, dried over magnesium sulfate and evaporated in vacuo. The residue was purified by column chromatography on silica gel with a mixture of n-hexane and benzene (1:1) as an eluent to give 2,2-diphenyl-2-(2-propynyl)acetaldehyde (0.46 g).

IR (Film): 3280, 3050, 1715, 1595 cm$^{-1}$

NMR (CDCl$_3$, δ): 1.92 (1H, t, J=2.7 Hz), 3.15 (2H, d, J=2.7 Hz), 7.16–7.54 (10H, m), 9.85 (1H, s)

Preparation 7

A solution of 2,2-diphenyl-2-(2-propynyl)acetaldehyde (83.0 g) in acetic acid (83 ml) was added dropwise to a solution of mercuric acetate (3.1 g) and sulfuric acid (18.3 g) in a mixture of acetic acid (300 ml) and water (75 ml) over a period of 2 hours at room temperature. The reaction mixture was poured into water and extracted with diethyl ether. The extract was washed successively with water and aqueous solution of sodium bicarbonate, and evaporated in vacuo. The residue was purified by column chromatography on silica gel with a mixture of n-hexane and ethyl acetate (5:1) as an eluent to give 3-acetyl-2,2-diphenylpropionaldehyde (48.9 g).

IR (Film): 3060, 1720, 1600 cm$^{-1}$

NMR (CDCl$_3$, δ): 2.05 (3H, s), 3.59 (2H, s), 7.14–7.45 (10H, m), 10.02 (1H, s)

Preparation 8

To a solution of 3-acetyl-2,2-diphenylpropionaldehyde (48.9 g) in a mixture of tetrahydrofuran (55 ml) and methanol (30 ml) was added 10% aqueous solution of potassium hydroxide (15 ml) at room temperature. The solution was stirred for 2 hours and evaporated in vacuo. To the residue was added brine and extracted with diethyl ether. The extract was washed with brine, dried over sodium sulfate and evaporated in vacuo. The residue was purified by column chromatography on silica gel with a mixture of n-hexane and ethyl acetate (5:1) as an eluent to give 4,4-diphenyl-2-cyclopenten-1-one (39.76 g).

IR (Film): 3080 1700 1665 1580 cm$^{-1}$

NMR (CDCl$_3$, δ): 3.12 (2H, s), 6.25 (1H, d, J=5.6 Hz), 7.06–7.49 (10H, m), 7.99 (1H, d, J=5.6 Hz)

Preparation 9

To a solution of 4,4-diphenyl-2-cyclopenten-1-one (0.30 g) in toluene (3 ml) was added a 1M solution of diisobutylaluminum hydride in n-hexane (2.0 ml) at −5° C. to 4° C. After being stirred for 20 minutes, ethyl acetate (3 ml) and 10% hydrochloric acid (2 ml) was added to the solution successively, and the mixture was extracted with ethyl acetate. The extract was washed with brine, dried over sodium sulfate and evaporated in vacuo. The residue was purified by column chromatography on silica gel with methylene chloride as an eluent to give 4,4-diphenyl-2-cyclopenten-1-ol (0.29 g).

IR (Neat): 3320 cm$^{-1}$

NMR (CDCl$_3$, δ): 2.41 (1H, dd, J=4.7 Hz and 13.8 Hz), 3.00 (1H, dd, J=6.9 Hz and 13.8 Hz), 4.90–5.10 (1H, m), 5.98 (1H, dd, J=2.0 Hz and 5.5 Hz), 6.38 (1H, dd, J=1.2 Hz and 5.5 Hz), 7.1–7.38 (10H, m)

Preparation 10

A mixture of 2,2-bis(p-tolyl)acetic acid (8.52 g), allyl alcohol (6.6 ml) and p-toluenesulfonic acid monohydrate (0.34 g) in toluene (25 ml) was refluxed for 20 hours with continuous removal of water with Dean-Stark apparatus. After being cooled, the mixture was poured into 1N Sodium hydroxide aqueous solution and extracted with ethyl acetate. The extract was washed with 1N sodium hydroxide aqueous solution, 1N hydrochloric acid and brine, dried over magnesium sulfate and evaporated in vacuo. The residue was purified by column chromatography on silica gel with methylene chloride as an eluent to give allyl 2,2-bis(p-tolyl)acetate (8.09 g).

IR (Film): 1730, 770, 750 cm$^{-1}$

NMR (CDCl$_3$, δ): 2.31 (6H, s), 4.60–4.70 (2H, m), 4.98 (1H, s), 5.15–5.30 (2H, m), 5.80–6.00 (1H, m), 6.95–7.36 (8H, m)

Preparation 11

A solution of allyl 2,2-bis(p-tolyl)acetate (8.00 g) in toluene (40 ml) was added dropwise to a suspension of sodium hydride (60% dispersion in mineral oil) (1.6 g) in toluene (30 ml) at 130° C. under nitrogen atmosphere, and the mixture was refluxed for 6 hours. After being cooled, the mixture was poured into cooled 1N hydrochloric acid, and extracted with ethyl acetate. The extract was washed with brine, dried over magnesium sulfate, and evaporated in vacuo to give 2,2-bis(p-tolyl)-4-pentenoic acid (4.41 g). It was used for the next reaction without further purification.

NMR (CDCl$_3$, δ): 2.32 (6H, s), 3.12 (2H, d, J=6.9 Hz), 4.89 (1H, s), 4.96 (1H, d, J=5.1 Hz), 5.45–5.70 (1H, m), 6.90–7.25 (8H, m)

Preparation 12

To a solution of 2,2-bis(p-tolyl)-4-pentenoic acid (8.17 g) in N,N-dimethylformamide (1.0 ml) and methylene chloride (45 ml) was added thionyl chloride (3.2 ml), and the solution was stirred at room temperature for 1 day. The solution was evaporated in vacuo and the residue was dissolved in methylene chloride (50 ml). The solution was added dropwise to a suspension of aluminum chloride (4.66 g) in methylene chloride (50 ml) with dry ice-acetone bath cooling under nitrogen atmosphere, and the resulting mixture was stirred at room temperature overnight. The mixture was poured into cooled 1N hydrochloric acid and extracted with ethyl acetate. The extract was washed with 1N hydrochloric acid, water, 1N sodium hydroxide, and brine, dried over magnesium sulfate, and evaporated in vacuo. The residue was purified by column chromatography on silica gel with a mixture of n-hexane and ethyl acetate (10:1~5:1) as an eluent to give 5,5-bis(p-tolyl)-2-cyclopenten-1-one (2.30 g).

mp: 61°–63° C.

IR (Nujol): 1690, 810, 780, 760, 720 cm$^{-1}$

NMR (CDCl$_3$, δ): 2.31 (6H, s), 3.47 (2H, t, J=2.5 Hz), 6.20–6.35 (1H, m), 7.10 (8H, s), 7.75–7.90 (1H, m)

The following compounds (Preparations 13 and 14) were obtained according to a similar manner to that of Preparation 9.

Preparation 13

5,5-Bis(p-tolyl)-2-cyclopenten-1-ol

IR (Film): 3550, 3430, 810, 790, 760, 740, 720 cm$^{-1}$

NMR (CDCl$_3$, δ): 1.22 (1H, d, J=9.5 Hz), 2.29 (3H, s), 2.32 (3H, s), 2.80–2.95 (1H, m), 3.30–3.46 (1H, m), 5.32–5.50 (1H, m), 5.85–5.95 (1H, m), 6.05–6.15 (1H, m), 7.00–7.35 (8H, m)

Preparation 14

4,4-Dimethyl-2-cyclopenten-1-ol bp: 41°–43° C./8 mmHg

IR (Neat): 3320, 1035 cm$^{-1}$

NMR (CDCl$_3$, δ): 1.05 (3H, s), 1.16 (3H, s), 1.53 (1H, dd, J=4.1 Hz and 13.5 Hz), 1.54 (1H, br s), 2.11 (1H, dd, J=7.3 Hz and 13.5 Hz), 4.84–4.95 (1H, m), 5.65 (1H, dd, J=2.0 Hz and 5.5 Hz), 5.76 (1H, dd, J=1.0 Hz and 5.5 Hz)

Preparation 15

A mixture of 4,4-diphenyl-2-cyclopenten-1-ol (0.30 g), and triphenylphosphine (0.43 g) in carbon tetrachloride (3 ml) was refluxed for 8 hours and cooled. To the mixture was added n-hexane (5 ml), and the mixture was stirred for 10 minutes at room temperature. The insoluble material was filtered off and the filtrate was condensed under reduced pressure. The residue was dissolved in methylene chloride, and to the solution was added silica gel (1 g). After being stirred for 10 minutes, silica gel was filtered off and the filtrate was evaporated in vacuo to give 4,4-diphenyl-2-cyclopentenyl chloride (0.30 g).

IR (Neat): 1595, 1490, 1445 cm$^{-1}$

NMR (CDCl$_3$, δ): 2.87 (1H, dd, J=4.7 Hz and 14.6 Hz), 3.22 (1H, dd, J=7.3 Hz and 14.6 Hz), 5.05–5.20 (1H, m), 5.98 (1H, dd, J=2.1 Hz and 5.5 Hz), 6.39 (1H, dd, J=1.2 Hz and 5.5 Hz), 7.10–7.40 (10H, m)

Preparation 16

A mixture of 2,2-dicyclopropylacetaldehyde (9.68 g), allyl alcohol (10.6 ml), toluene (9.7 ml) and p-toluenesulfonic acid (0.05 g) was heated under a 20 cm packed distillation topped by a Dean-Stark trap for 6 days. During this period, 0.9 ml of aqueous layer separated. Distillation of the reaction mixture gave, after removal of toluene and a small forerun, 2,2-dicyclopropyl-4-pentenal (4.90 g).

bp: 43°–47° C./0.2 mmHg

IR (Neat): 1720 cm$^{-1}$

NMR (CDCl$_3$, δ): 0.40–0.58 (8H, m), 0.68–0.85 (2H, m), 2.12–2.30 (2H, m), 5.00–5.18 (2H, m), 5.75–6.00 (1H, m), 9.47 (1H, s)

Preparation 17

A suspension of cuprous chloride (2.25 g), and palladium dichloride (0.81 g) in N,N-dimethylformamide (12 ml) and water (2.2 ml) was stirred at room temperature for 1 hour while oxygen was bubbling through the suspension. To this mixture, a solution of 2,2-dicyclopropyl-4-pentenal (3.74 g) in N,N-dimethylformamide (10 ml) was added at 22° C. to 35° C. and the suspension was stirred for 4 hours at room temperature with bubbling of oxygen through the suspension. After diluting the suspension with water (110 ml), the aqueous layer was extracted with diethyl ether. The extract was washed with water, dried over sodium sulfate and evaporated in vacuo. The residue was purified by distillation under reduced pressure to give 4-oxo-2,2-dicyclopropylpentanal (1.98 g).

bp: 80°–83° C./0.50 mmHg

IR (Neat): 1720 cm$^{-1}$

NMR (CDCl$_3$, δ): 0.24–0.60 (8H, m), 0.80–1.00 (2H, m), 2.15 (3H, s), 2.69 (2H, s), 9.61 (1H, s)

Preparation 18

To a mixture of 5% aqueous solution of potassium hydroxide (4.7 ml) and tetrahydrofuran (4.7 ml) was added a solution of 4-oxo-2,2-dicyclopropylpentanal (1.88 g) in diethyl ether (9.4 ml). The mixture was heated at 38° C. to 45° C. for 3 hours and cooled. The aqueous layer was saturated with sodium chloride. The mixture was extracted with diethyl ether and the extract was washed with brine, dried over sodium sulfate, and evaporated in vacuo. The residue was purified by distillation under reduced pressure to give 4,4-dicyclopropyl-2-cyclopenten-1-one (1.55 g).

bp: 101°–105° C./5 mmHg

IR (Neat): 1710 cm$^{-1}$

NMR (CDCl$_3$, δ): 0.10–0.54 (8H, m), 0.92–1.12 (2H, m), 2.04 (2H, s), 6.07 (1H, d, J=5.7 Hz), 7.20 (1H, d, J=5.7 Hz)

Preparation 19

To a solution of 4,4-dicyclopropyl-2-cyclopenten-1-one (1.88 g) in diethyl ether (20 ml) was added diisobutylaluminum hydride (0.94N in n-hexane, 14 ml) at −70° C. to −64° C. under nitrogen atmosphere. After being stirred for 20 minutes, ethyl acetate (6 ml) was added thereto and the solution was acidified with dil. hydrochloric acid and extracted with diethyl ether. The extract was washed with brine, dried over sodium sulfate and evaporated in vacuo to give 4,4-dicyclopropyl-2-cyclopenten-1-ol (0.53 g). Since this compound was not so stable, it was used in the next reaction without purification.

EXAMPLE 11

To a solution of 5,5-diphenyl-2-cyclopenten-1-ol (0.30 g) in acetone were added methanesulfonyl chloride (0.12 ml) and triethylamine (0.21 ml) at 1° C. to 3° C. After being stirred for 15 minutes sodium iodide (0.23 g) was added thereto and the mixture was stirred for 10 minutes. To the mixture was added t-butylamine (2.67 ml) at −1° C. to 2° C. and the mixture was stirred at room temperature overnight. Cold water was added to the mixture and the mixture was extracted with ethyl acetate. The extract was washed with brine, dried over sodium sulfate and evaporated in vacuo. The residue was dissolved in ethyl acetate. To the solution was added 3N hydrochloric acid (1 ml) with cooling in an ice bath, and the mixture was stirred for 30 minutes. The resulting precipitates were collected by filtration, washed with water, ethyl acetate successively and dried to give N-t-butyl-4,4-diphenyl-2-cyclopentenylamine hydrochloride (0.31 g).

mp 265°–267° C. (dec.)

IR (Nujol): 2730, 2690, 2530, 2490, 2430 cm$^{-1}$

NMR (DMSO-d$_6$, δ): 1.37 (9H, s), 2.51 (1H, dd, J=8.1 Hz and 13.3 Hz), 3.34 (1H, dd, J=7.2 Hz and 13.3 Hz), 4.44 (1H, br m), 6.16 (1H, d, J=5.6 Hz), 6.72 (1H, d, J=5.6 Hz), 7.10–7.38 (10H, m), 8.89 (1H, br s), 9.52 (1H, br s)

The following compounds (Examples 12 to 23) were obtained according to a similar manner to that of Example 11.

EXAMPLE 12

N-Methyl-4,4-diphenyl-2-cyclopentenylamine hydrochloride mp: 168°–169° C.

IR (Nujol): 2680, 2430, 1600, 770, 750, 700 cm$^{-1}$

NMR (DMSO-d$_6$, δ): 2.30 (1H, dd, J=8.2 Hz and 13.4 Hz), 2.56 (3H, s), 3.24 (1H, dd, J=7.0 Hz and 13.4 Hz), 4.20–4.35 (1H, m), 6.06 (1H, dd, J=5.7 Hz and 1.5 Hz), 6.78 (1H, dd, J=5.7 Hz and 1.9 Hz), 7.10–7.45 (10H, m), 9.21 (2H, broad s)

EXAMPLE 13

N-Ethyl-4,4-diphenyl-2-cyclopentenylamine hydrochloride mp: 209°–210° C. (recrystallized from isopropyl alcohol-ethyl acetate)

IR (Nujol): 2680, 2450, 1595, 790, 770, 750, 700 cm$^{-1}$

NMR (DMSO-d$_6$, δ): 1.22 (3H, t, J=7.2 Hz), 2.33 (1H, dd, J=13.3 Hz and 8.3 Hz), 3.00 (2H, qd, J=7.2 Hz and 1.8 Hz), 3.25 (1H, dd, J=13.3 Hz and 7.0 Hz), 4.25–4.35 (1H, m), 6.07 (1H, dd, J=5.7 Hz and 1.4 Hz), 6.76 (1H, dd, J=5.7 Hz and 1.9 Hz), 7.12–7.46 (10H, m), 9.25 (2H, broad s)

EXAMPLE 14

N-Butyl-4,4-diphenyl-2-cyclopentenylamine hydrochloride mp: 158.5°–159° C. (recrystallized from a mixture of n-hexane, ethyl acetate, and acetone)

IR (Nujol): 2770, 2710, 2660, 2610, 2580, 2550, 2480, 2440, 1600 cm$^{-1}$

NMR (DMSO-d$_6$, δ): 0.88 (3H, t, J=7.5 Hz), 1.33 (2H, sextet, J=7.5 Hz), 1.61 (2H, quintet, J=7.5 Hz), 2.35 (1H, dd, J=8.5 Hz and 13.5 Hz), 2.90 (2H, m), 3.26 (1H, dd, J=7.0 Hz and 13.5 Hz), 4.32 (1H, m), 6.09 (1H, d, J=5.5 Hz), 6.76 (1H, dd, J=2.0 Hz and 5.5 Hz), 7.1–7.4 (10H, m), 9.25 (2H, br s)

EXAMPLE 15

N,N-Dimethyl-4,4-diphenyl-2-cyclopentenylamine hydrochloride mp: 189°–190° C. (recrystallized from isopropyl alcohol-acetone)

IR (Nujol): 2550, 2430, 780, 760, 700 cm$^{-1}$

NMR (DMSO-d$_6$, δ): 2.44 (1H, dd, J=13.6 Hz and 8.1 Hz), 2.74 (6H, s), 3.20 (1H, dd, J=13.6 Hz and 7.1 Hz), 4.40–4.55 (1H, m), 6.14 (1H, dd, J=1.6 Hz and 5.8 Hz), 6.85 (1H, dd, J=2.0 Hz and 5.8 Hz), 7.20–7.40 (10H, m), 10.73 (1H, broad s)

EXAMPLE 16

N,N-Diethyl-4,4-diphenyl-2-cyclopentenylamine hydrochloride mp: 186°–187° C. (recrystallized from isopropyl alcohol-ethyl acetate)

IR (Nujol): 2520, 2470, 1600, 790, 750, 700 cm$^{-1}$

NMR (DMSO-d$_6$, δ): 1.23 (6H, t, J=7.12 Hz), 2.35–2.47 (1H, m), 3.02–3.30 (5H, m), 4.53–4.72 (1H, m), 6.13 (1H, d, J=5.8 Hz), 6.89 (1H, d, J=5.8 Hz), 7.18–7.52 (10H, m), 10.03 (1H, broad s)

EXAMPLE 17

N-Benzyl-N-methyl-4,4-diphenyl-2-cyclopentenylamine hydrochloride mp: 162°–165° C.

IR (Nujol): 3050, 2500, 780, 760, 750, 700 cm$^{-1}$

NMR (DMSO-d$_6$, δ): 2.35–2.70 (1H, m), 3.10–3.45 (1H, m), 3.34 (3H, s), 4.10–4.30 (1H, m), 4.40–4.70 (2H, m), 6.15–6.30 (1H, m), 6.75–7.00 (1H, m), 7.10–7.40 (10H, m), 7.40–7.55 (3H, m), 7.55–7.70 (2H, m), 10.80–11.20 (1H, m)

EXAMPLE 18

N-Benzyl-4,4-diphenyl-2-cyclopentenylamine hydrochloride mp: 201°–204° C. (recrystallized from methanol-isopropyl alcohol-ethyl acetate)

IR (Nujol): 1600, 1580, 760, 700 cm$^{-1}$

NMR (DMSO-d$_6$, δ): 2.45 (1H, dd, J=13.2 Hz and 8.6 Hz), 3.28 (1H, dd, J=13.2 Hz and 6.8 Hz), 4.21 (2H, broad s), 4.30–4.50 (1H, m), 6.15 (1H, d, J=5.7 Hz), 6.77 (1H, dd, J=5.7 Hz and 1.7 Hz), 7.10–7.35 (10H, m), 7.35–7.55 (3H, m), 7.55–7.80 (2H, m), 9.82 (2H, broad s)

EXAMPLE 19

N-(1,1-Dimethyl-2-hydroxyethyl)-4,4-diphenyl-2-cyclopentenylamine methanesulfonate mp: 176°–177° C.

IR (Nujol): 3400, 1600 cm$^{-1}$

NMR (CDCl$_3$, δ): 1.39 (6H, s), 2.60 (3H, s), 2.77 (1H, dd, J=13.3 Hz and 8.5 Hz), 3.23 (1H, dd, J=13.3 Hz and 6.9 Hz), 3.62 (2H, s), 4.35 (1H, br s), 6.19 (1H, dd, J=5.7 Hz and 1.0 Hz), 6.43 (1H, dd, J=5.7 Hz and 2.0 Hz), 7.12–7.36 (10H, m), 8.17–8.56 (2H, m)

EXAMPLE 20

N-[1,1-Dimethyl-2-(N-methylbenzylamino)ethyl]-4,4-diphenyl-2-cyclopentenylamine dihydrochloride mp: 196°–197° c (dec.) (recrystallized from ethanol-ethyl acetate)

IR (Nujol): 2750, 2600, 2500, 1600, 1580, 790, 750, 700 cm$^{-1}$

NMR (DMSO-d$_6$, δ): 1.40 (3H, s), 1.59 (3H, s), 2.45–2.70 (1H, m), 2.89 (3H, s), 2.82 (1H, dd, J=6.9 Hz and 13.2 Hz), 3.35–3.90 (2H, m), 4.20–4.60 (1H, m), 4.45 (2H, s), 6.11 (1H, d, J=5.3 Hz), 6.74 (1H, d, J=5.5 Hz), 6.95–7.85 (15H, m), 9.64 (1H, broad s), 10.23 (1H, broad s), 11.03 (1H, broad s)

EXAMPLE 21

N-(1-Ethylcyclohexan-1-yl)-4,4-diphenyl-2-cyclopentenylamine hydrochloride mp: 228°–234° C. (dec.) (recrystallized from methanol-ethanol-ethyl acetate)

IR (Nujol): 1580, 780, 770, 700 cm$^{-1}$

NMR (DMSO-d$_6$, δ): 0.89 (3H, t, J=7.4 Hz), 1.00–2.10 (12H, m), 2.58 (1H, dd, J=13.4 Hz and 8.2 Hz), 3.28 (1H, dd, J=13.4 Hz and 6.1 Hz), 4.42 (1H, broad s), 6.14 (1H, broad d, J=5.7 Hz), 6.73 (1H, broad d, J=3.9 Hz), 7.10–7.50 (10H, m), 8.55–8.80 (1H, m), 8.90–9.20 (1H, m)

EXAMPLE 22

4-(4,4-Diphenyl-2-cyclopentenyl)morpholine hydrochloride mp: 285°–288° C. (dec.) (recrystallized from methanol)

IR (Nujol): 2520, 2440, 790, 760, 700 cm$^{-1}$

DMSO-d$_6$, δ): 3.00–3.82 (8H, m), 3.90–4.08 (2H, m), 4.48–4.60 (1H, m), 6.19–6.30 (1H, m), 6.84–6.95 (1H, m), 7.15–7.42 (10H, m), 10.50–10.72 (1H, broad s)

EXAMPLE 23

N-t-Butyl-4,4-bis(p-tolyl)-2-cyclopentenylamine hydrochloride mp: 265°–267° C. (recrystallized from ethanol-isopropyl alcohol)

IR (Nujol): 2760, 2630, 820, 800, 720 cm$^{-1}$

NMR (DMSO-d$_6$, δ): 1.36 (9H, s), 2.25 (3H, s), 2.26 (3H, s), 2.46 (1H, dd, J=7.9 Hz and 13.4 Hz), 3.26 (1H, dd, J=7.1 Hz and 13.4 Hz), 4.39 (1H, broad s), 6.10 (1H, dd, J=1.3 Hz and 5.7 Hz), 6.65 (1H, dd, J=1.8 Hz and 5.7 Hz), 7.09 (4H, s), 7.12 (4H, s), 8.82 (1H, broad s), 9.38 (1H, broad s)

EXAMPLE 24

To a solution of 4,4-dicyclopropyl-2-cyclopenten-1-ol (0.52 g) in acetone (5 ml) were added methanesulfonyl chloride (0.27 ml) and triethylamine (0.49 ml) with ice bath cooling. After being stirred for 10 minutes, sodium iodide (0.52 g) was added thereto, and the mixture was stirred for 10 minutes. To the mixture was added t-butylamine (6.4 ml), and the mixture was stirred at room temperature overnight. The solvent was evaporated in vacuo, and then cold water was added thereto, and the mixture was extracted with ethyl acetate. The extract was washed with brine, dried over sodium sulfate, and evaporated in vacuo. The residue was dissolved in ethyl acetate, and hydrogen chloride in ethanol (8.9N, 0.5 ml) was added thereto, and evaporated in vacuo. The residue was crystallized from diethyl ether to give N-t-butyl-4,4-dicyclopropyl-2-cyclopentenylamine hydrochloride (0.51 g). These crystals were recrystallized from a mixture of isopropyl alcohol and ethyl acetate to give pure one (0.41 g).

mp: 202.5°–203.5° C.

IR (Nujol): 2750, 2625, 2500, 2455, 2430, 1580 cm$^{-1}$

NMR (CDCl$_3$, δ): −0.10–0.15 (2H, m), 0.15–0.64 (6H, m), 0.64–0.85 (1H, m), 0.96–1.15 (1H, m), 1.50 (9H, s), 2.19 (1H, dd, J=7.6 Hz and 12.9 Hz), 2.27 (1H, dd, J=8.0 Hz and 12.9 Hz), 4.08–4.28 (1H, m), 5.41 (1H, dd, J=2.2 Hz and 5.8 Hz), 6.22 (1H, dd, J=1.5 Hz and 5.8 Hz), 9.37 (2H, broad s)

EXAMPLE 25

A mixture of 4,4-diphenyl-2-cyclopenten-1-ol (0.30 g) and carbon tetrabromide (0.55 g) in diisopropyl ether (3 ml) was refluxed for 30 minutes. After being cooled, n-hexane (10 ml) and diisopropyl ether (2 ml) was added thereto and the insoluble material was filtered off. The filtrate was evaporated in vacuo below 30° C. To the residue acetone (4 ml) and t-butylamine (2 ml) were added and refluxed for 30 minutes, and cooled. The mixture was condensed under reduced pressure and was purified by column chromatography on silica-gel with a mixture of chloroform and methanol as an eluent to give N-t-butyl-4,4-diphenyl-2-cyclopentenylamine (0.26 g).

The physical data were identified with those of the compound of Example 1.

EXAMPLE 26

N-t-Butyl-4,4-dimethyl-2-cyclopentenylamine hydrochloride was obtained according to a similar manner to that of Example 25.

mp: 194° C. (dec.) (recrystallized from a mixture of diethyl ether and chloroform)

IR (Nujol): 3400, 2760, 2690, 2640, 2470 cm$^{-1}$

NMR (CDCl$_3$, δ): 1.05 (3H, s), 1.26 (3H, s), 1.51 (9H, s), 2.17 (1H, dd, J=8.0 Hz and 13.3 Hz), 2.37 (1H, dd, J=7.3 Hz and 13.3 Hz), 4.26–4.45 (1H, m), 5.78 (1H, dd, J=2.1 Hz and 5.6 Hz), 6.03 (1H, dd, J=1.7 Hz and 5.6 Hz), 9.35 (2H, br s)

EXAMPLE 27

A mixture of 4,4-diphenyl-2-cyclopentenyl chloride (0.20 g), t-butylamine (2 ml) and a catalytic amount of sodium iodide in acetone (4 ml) was refluxed for 15 hours and cooled. The mixture was evaporated in vacuo and water was added thereto extracted with ethyl acetate. The extract was washed with brine, dried over sodium sulfate and evaporated in vacuo. The residue was purified by column chromatography on silica gel with a mixture of chloroform and methanol as an eluent to give N-t-butyl-4,4-diphenyl-2-cyclopentenylamine (0.15 g).

The physical data of this compound were identified with those of the compound of Example 1.

EXAMPLE 28

A mixture of 4,4-diphenyl-2-cyclopentenyl chloride (0.30 g), t-butylamine (1.24 ml), a catalytic amount of sodium iodide and 18-crown-6 in methylene chloride (3 ml) was refluxed for 47 hours and cooled. The solvent was removed off in vacuo, and water was added thereto, and the mixture was extracted with ethyl acetate. The extract was washed with brine, dried over sodium sulfate and evaporated under reduced pressure. To the residue were added ethyl acetate (5 ml) and 3N hydrochloric acid (2 ml) with cooling in an ice bath, and the mixture was stirred for 3 hours. The precipitate was collected by filtration, washed with ethyl acetate, water, ethyl acetate successively and dried to give N-t-butyl-4,4-diphenyl-2-cyclopentenylamine hydrochloride (0.28 g).

The physical data of this compound were identified with those of the compound of Example 11.

EXAMPLE 29

A mixture of 4,4-diphenyl-2-cyclopentenyl chloride (0.26 g) and sodium iodide (0.15 g) in acetone (5 ml) was refluxed for 90 minutes. The insoluble material was filtered off. To the filtrate were added t-butylamine (1.5 ml) and acetone (5 ml). The solution was refluxed for 2 hours and cooled. The solvent was removed off in vacuo and water was added thereto, extracted with ethyl acetate. The extract was washed with brine, dried over sodium sulfate, and evaporated under reduced pressure. The residue was purified by column chromatography on silica gel with a mixture of chloroform and methanol as an eluent to give N-t-butyl-4,4-diphenyl-2-cyclopentenylamine (0.25 g).

The physical data of this compound were identified with those of the compound of Example 1.

EXAMPLE 30

To a solution of 4,4-diphenyl-2-cyclopentenyl azide (0.30 g) in acetone (3 ml) was added triphenylphosphine (0.33 g) at room temperature and refluxed for 21 hours. After being cooled, the solvent was removed under reduced pressure and a solution of sodium borohydride (0.22 g), in methanol (3 ml) was added thereto. After being stirred for 20 minutes, brine and ethyl acetate were added. The organic layer was separated, washed with brine, dried over magnesium sulfate and evaporated in vacuo. The residue was purified by flash column chromatography on silica gel with a mixture of chloroform and methanol as an eluent to give N-isopropyl-4,4-diphenyl-2-cyclopentenylamine (0.26 g).

NMR (CDCl$_3$, δ): 1.07 (3H, d, J=6.20 Hz), 1.09 (3H, d, J=6.20 Hz), 1.90 (1H, br s), 2.15 (1H, dd, J=7.05 Hz and 13.14 Hz), 1.85–3.14 (2H, m), 4.00–4.15 (1H, m), 5.60 (1H, dd, J=5.61 Hz and 1.74 Hz), 6.28 (1H, dd, J=5.61 Hz and 1.84 Hz), 7.10–7.40 (10H, m)

To a solution of the free amine compound obtained above (0.26 g) in chloroform was added methanesulfonic acid (92 mg) in methanol and evaporated in vacuo. The residue was triturated with a mixture of diethyl ether and ethyl acetate to give its methanesulfonate (0.26 g).

mp: 148°–150° C.

IR (Nujol): 1610, 1490 cm$^{-1}$

NMR (CDCl$_3$, δ): 1.38 (3H, d, J=6.2 Hz), 1.39 (3H, d, J=6.2 Hz), 2.52 (3H, s), 2.64 (1H, dd, J=8.7 Hz and 13.0 Hz), 3.19 (1H, dd, J=6.7 Hz and 13.0 Hz), 3.20–3.50 (1H, m), 4.35 (1H, br s), 6.12 (1H, d, J=5.7 Hz), 6.42 (1H, d, J=5.7 Hz), 7.10–7.40 (10H, m), 8.75 (2H, br s)

EXAMPLE 31

A mixture of 4,4-diphenyl-2-cyclopentenyl chloride (0.60 g), 4-diethylamino-1,1-dimethyl-2-butynylamine (0.79 g) and a catalytic amount of sodium iodide in acetone (5 ml) was refluxed for 8 hours. After being cooled, the solvent was removed off under reduced pressure and the residue was purified with column chromatography on silica gel with a mixture of chloroform and methanol as an eluent to give N-[4-diethylamino-1,1-dimethyl-2-butynyl]-4,4-diphenyl-2-cyclopentenylamine (0.54 g). The free amine obtained above was dissolved in chloroform, and to the solution was added hydrogen chloride in methanol (0.18 g/ml, 1 ml). The solution was evaporated in vacuo and triturated with a mixture of ethanol and isopropyl alcohol to give its hydrochloride (0.45 g).

mp: 225° C. (dec.) (recrystallized from ethanol)

IR (Nujol): 2725, 2300 cm$^{-1}$

NMR (D$_2$O, δ): 1.26 (6H, t, J=7.3 Hz), 1.77 (6H, s), 2.57 (1H, dd, J=8.2 Hz and 13.4 Hz), 3.23 (4H, q, J=7.3 Hz), 3.47 (1H, dd, J=7.0 Hz and 13.4 Hz), 4.17 (2H, s), 4.60–4.80 (1H, m), 6.15 (1H, dd, J=1.2 Hz and 5.7 Hz), 6.85 (1H, dd, J=1.8 Hz and 5.7 Hz), 7.24–7.50 (10H, m)

EXAMPLE 32

To a solution of 2-cyclopenten-1-one (2.0 g) in diethyl ether (20 ml) was added diisobutylaluminum hydride (0.94M in n-hexane, 28.5 ml) at −70° C. to −60° C. under nitrogen atmosphere. After being stirred for 1 hour, ethyl acetate (11.9 ml) was added thereto, and the solution was acidified with dil. hydrochloric acid, and extracted with ethyl acetate. The extract was washed with brine, dried over magnesium sulfate, and the solvent was removed off by distillation. The residue was dissolved in acetone (50 ml). To the solution were added methanesulfonyl chloride (1.88 ml) and triethylamine (3.39 ml) with ice bath cooling. After being stirred for 10 minutes, sodium iodide (3.63 g) was added thereto, and the mixture was stirred for 10 minutes. To the mixture was added t-butylamine (49 ml), and the mixture was stirred at room temperature overnight. The solvent was removed off by distillation, and then cold water was added thereto, and the mixture was extracted with ethyl acetate. To the extract was added hydrogen chloride in ethanol (8.9N, 3 ml), and condensed under reduced pressure. The residue was crystallized from a mixture of diethyl ether and isopropyl alcohol to give t-butylamine hydrochloride (0.40 g). The resultant salt was removed off by filtration, and the filtrate was evaporated in vacuo. The residue was crystallized from a mixture of diethyl ether and ethyl acetate to give N-t-butyl-2-cyclopentenylamine hydrochloride (0.74 g). These crystals were recrystallized from a mixture of isopropyl alcohol and ethyl acetate to give pure compound (0.26 g).

mp: 178°-180° C. (dec.)

IR (Nujol): 2770, 2650, 2500, 2440 cm$^{-1}$

NMR (CDCl$_3$, δ): 1.52 (9H, s), 2.20-2.64 (3H, m), 2.64-2.90 (1H, m), 4.24 (1H, br s), 6.00-6.18 (2H, m), 9.24 (2H, br s)

EXAMPLE 33

To a solution of N-t-butyl-3,3-diphenylcyclopentylamine (0.49 g) in chloroform and methanol was added a solution of methanesulfonic acid (0.16 g) in methanol. The solvent was evaporated in vacuo and ethyl acetate was added. After standing for 2 hours, the resulting precipitate was collected to give N-t-butyl-3,3-diphenylcyclopentylamine methanesulfonate (0.51 g).

mp: 243°-244° C.

IR (Nujol): 1610, 1490 cm$^{-1}$

NMR (DMSO-d$_6$, δ): 1.30 (9H, s), 1.88-2.40 (4H, m), 2.32 (3H, s), 2.60-2.78 (1H, m), 3.20-3.36 (1H, m), 3.48-3.70 (1H, m), 7.05-7.50 (10H, m), 8.45 (2H, br s)

EXAMPLE 34

To a solution of 4,4-diphenyl-2-cyclopenten-1-one (0.40 g), t-butylamine (0.75 g) in methylene chloride (9 ml) was added dropwise a solution of titanium tetrachloride (0.50 g) in methylene chloride (5 ml) at −70° C. to −60° C. After being stirred for 2 hours, sodium borohydride (0.35 g) and methanol (6 ml) were added successively at 0° C. After being stirred for 0.5 hour, the precipitate was filtered off using celite and the filtrate was condensed under reduced pressure. To the residue, 1N sodium hydroxide aqueous solution was added and extracted with ethyl acetate. The extract was washed with brine, dried over magnesium sulfate and evaporated in vacuo. The residue was purified by column chromatography on silica gel with a mixture of chloroform and methanol as an eluent to give N-t-butyl-4,4-diphenyl-2-cyclopentenylamine (0.13 g) and N-t-butyl-3,3-diphenylcyclopentylamine (0.19 g) respectively.

N-t-Butyl-4,4-diphenyl-2-cyclopentenylamine

NMR (CDCl$_3$, δ): 0.80-1.40 (1H, br m), 1.12 (9H, s), 2.04 (1H, dd, J=7.6 Hz and 13.0 Hz), 3.09 (1H, dd, J=6.8 Hz and 13.0 Hz), 3.94-4.10 (1H, m), 5.85 (1H, dd, J=1.7 Hz and 5.6 Hz), 6.21 (1H, dd, J=2.0 Hz and 5.6 Hz), 7.09-7.38 (10H, m)

N-t-Butyl-3,3-diphenylcyclopentylamine

NMR (CDCl$_3$, δ): 1.03 (9H, s), 1.49-1.72 (1H, m), 1.93-2.63 (5H, m), 2.74-2.89 (1H, m), 3.14-3.37 (1H, m), 7.02-7.14 (10H, m)

EXAMPLE 35

N-t-Butyl-4,4-diphenyl-2-cyclohexenylamine methanesulfonate was obtained according to a similar manner to that of Example 34.

mp: 227°-229° C. (recrystallized from a mixture of ethanol and diethyl ether)

NMR (CDCl$_3$, δ): 1.43 (9H, s), 1.75-2.33 (4H, m), 2.50 (3H, s), 3.60-3.90 (1H, m), 6.09 (1H, dd, J=10 Hz and 2 Hz), 6.36 (1H, d, J=10 Hz), 7.00-7.30 (10H, m), 8.30 (2H, br s)

EXAMPLE 36

To a solution of 4,4-diphenylcyclohexan-1-one (1.15 g) and t-butylamine (2.01 g) in methylene chloride (20 ml) was added dropwise a solution of titanium tetrachloride (0.66 g) in methylene chloride (6 ml) at −70° C. to −50° C. After being stirred for 30 minutes, sodium borohydride (0.34 g) and methanol (20 ml) were added to the mixture. After being stirred for 30 minutes, water (5 ml) was added to the mixture and the precipitate was filtered off using celite. The filtrate was condensed under reduced pressure and extracted with ethyl acetate. The extract was washed with brine, dried over sodium sulfate and evaporated in vacuo. The residue (1.47 g) was dissolved in ethyl acetate and the solution was added to a solution of methanesulfonic acid (441 mg) in methanol (3 ml). After standing overnight at room temperature, the resulting precipitate was collected to give N-t-butyl-4,4-diphenylcyclohexylamine methanesulfonate (1.20 g).

mp: 253°-255° C.

NMR (CDCl$_3$, δ): 1.36 (9H, s), 1.60-2.95 (9H, m), 2.35 (3H, s), 6.96-7.35 (10H, m), 7.90 (2H, br s)

EXAMPLE 37

N-t-Butyl-3,3-diphenylcyclobutylamine methansulfonate was obtained according to a similar manner to that of Example 36.

mp: 197°-198° C.

IR (Nujol): 1590, 1485 cm$^{-1}$

NMR (CDCl$_3$, δ): 1.37 (9H, s), 2.33 (3H, s), 3.22 (4H, d, J=8.29 Hz), 3.67 (1H, pentet, J=8.29 Hz), 7.06-7.43 (10H, m), 8.71 (2H, s)

The following compounds (Examples 38 to 55) were obtained according to a similar manner to that of Example 34.

EXAMPLE 38

N-Methyl-4,4-diphenyl-2-cyclopentenylamine hydrochloride

IR (Nujol): 2680, 2430, 1600, 770, 750, 700 cm$^{-1}$

EXAMPLE 39

N-Ethyl-4,4-diphenyl-2-cyclopentenylamine hydrochloride

IR (Nujol): 2680, 2450, 1595, 790, 770, 750, 700 cm$^{-1}$

EXAMPLE 40

N-Butyl-4,4-diphenyl-2-cyclopentenylamine hydrochloride

IR (Nujol): 2770, 2710, 2660, 2610, 2580, 2550, 2480, 2440, 1600 cm$^{-1}$

EXAMPLE 41

N,N-Dimethyl-4,4-diphenyl-2-cyclopentenylamine hydrochloride

IR (Nujol): 2550, 2430, 780, 760, 700 cm$^{-1}$

EXAMPLE 42

N,N-Diethyl-4,4-diphenyl-2-cyclopentenylamine hydrochloride

IR (Nujol): 2520, 2470, 1600, 790, 750, 700 cm$^{-1}$

EXAMPLE 43

N-Benzyl-N-methyl-4,4-diphenyl-2-cyclopentenylamine hydrochloride

IR (Nujol): 3050, 2500, 780, 760, 750, 700 cm$^{-1}$

EXAMPLE 44

N-Benzyl-4,4-diphenyl-2-cyclopentenylamine hydrochloride

IR (Nujol): 1600, 1580, 760, 700 cm$^{-1}$

EXAMPLE 45

N-(1,1-Dimethyl-2-hydroxyethyl)-4,4-diphenyl-2-cyclopentenylamine methanesulfonate
IR (Nujol): 3400, 1600 cm$^{-1}$

EXAMPLE 46

N-[1,1-Dimethyl-2-(N-methylbenzylamino)ethyl]-4,4-diphenyl-2-cyclopentenylamine dihydrochloride
IR (Nujol): 2750, 2600, 2500, 1600, 1580, 790, 750, 700 cm$^{-1}$

EXAMPLE 47

N-(1-Ethylcyclohexan-1-yl)-4,4-diphenyl-2-cyclopentenylamine hydrochloride
IR (Nujol): 1580, 780, 770, 700 cm$^{-1}$

EXAMPLE 48

4-(4,4-Diphenyl-2-cyclopentenyl)morpholine hydrochloride
IR (Nujol): 2520, 2440, 790, 760, 700 cm$^{-1}$

EXAMPLE 49

N-t-Butyl-4,4-bis(p-tolyl)-2-cyclopentenylamine hydrochloride
IR (Nujol): 2760, 2630, 820, 800, 720 cm$^{-1}$

EXAMPLE 50

N-t-Butyl-4,4-dichloropropyl-2-cyclopentenylamine hydrochloride
IR (Nujol): 2750, 2625, 2500, 2455, 2430, 1580 cm$^{-1}$

EXAMPLE 51

N-t-Butyl-4,4-dimethyl-2-cyclopentenylamine hydrochloride
IR (Nujol): 3400, 2760, 2690, 2640, 2470 cm$^{-1}$

EXAMPLE 52

N-Isopropyl-4,4-diphenyl-2-cyclopentenylamine methanesulfonate
IR (Nujol): 1610, 1490 cm$^{-1}$

EXAMPLE 53

N-[4-Diethylamino-1,1-dimethyl-2-butynyl]-4,4-diphenyl-2-cyclopentenylamine hydrochloride
IR (Nujol): 2725, 2300 cm$^{-1}$

EXAMPLE 54

N-t-Butyl-2-cyclopentenylamine hydrochloride
IR (Nujol): 2770, 2650, 2500, 2440 cm$^{-1}$

EXAMPLE 55

1-(4,4-Diphenyl-2-cyclopentenyl)piperazine dihydrochloride
IR (Nujol): 1590, 770, 750, 700 cm$^{-1}$

EXAMPLE 56

1-(4,4-Diphenyl-2-cyclopentenyl)piperazine dihydrochloride was obtained by reacting 5,5-diphenyl-2-cyclopenten-1-ol and 1-formylpiperazine according to a similar manner to that of Example 11 to give 1-(4,4-diphenyl-2-cyclopentenyl)-4-formylpiperazine, then eliminating formyl group thereof in a conventional manner.
mp: 244° C. (dec.)
IR (Nujol): 1590, 770, 750, 700 cm$^{-1}$
NMR (CD$_3$OD, δ): 2.58 (1H, dd, J=13.9 Hz and 7.7 Hz), 3.39 (1H, dd, J=13.9 Hz and 7.5 Hz), 3.63 (8H, broad s), 4.76 (1H, pseudo t, J=7.5 Hz), 6.17 (1H, dd, J=5.7 Hz and 1.6 Hz), 6.87 (1H, dd, J=5.7 Hz and 1.9 Hz), 7.10-7.40 (10H, m)

The following compounds (Examples 57 to 60) were obtained according to a similar manner to that of Example 11 or 25 or 27.

EXAMPLE 57

N-t-Butyl-3,3-diphenylcyclopentylamine
NMR (CDCl$_3$, δ): 1.03 (9H, s), 1.49–1.72 (1H, m), 1.93–2.63 (5H, m), 2.74–2.89 (1H, m), 3.14–3.37 (1H, m), 7.02–7.14 (10H, m)

EXAMPLE 58

N-t-Butyl-4,4-diphenylcyclohexenylamine methanesulfonate
mp: 227°–229° C.

EXAMPLE 59

N-t-Butyl-4,4-diphenylcyclohexylamine methanesulfonate
mp: 253°–255° C.

EXAMPLE 60

N-t-Butyl-3,3-diphenylcyclobutylamine methanesulfonate
IR (Nujol): 1590, 1485 cm$^{-1}$ The following compounds (Examples 61 to 63) were obtained according to a similar manner to that of Example 8.

EXAMPLE 61

N-t-Butyl-3,3-diphenylcyclopentylamine
NMR (CDCl$_3$, δ): 1.03 (9H, s), 1.49–1.72 (1H, m), 1.93–2.63 (5H, m), 2.74–2.89 (1H, m), 3.14–3.37 (1H, m), 7.02–7.14 (10H, m)

EXAMPLE 62

N-t-Butyl-4,4-diphenylcyclohexylamine methanesulfonate
mp: 253°–255° C.

EXAMPLE 63

N-t-Butyl-3,3-diphenylcyclobutylamine methanesulfonate
IR (Nujol): 1590, 1485 cm$^{-1}$

Preparation 20

To a suspension of 5,5-diphenyl-2-cyclopenten-1-ol (5.0 g), dimethyl D-tartrate (0.49 g), molecular sieves 4A (activated powder 0.5 g) in methylene chloride (50 ml) was added titanium(IV) isopropoxide (0.63 ml) under nitrogen atmosphere with cooling in a dry-ice acetone bath. After being stirred for 30 minutes, t-butyl hydroperoxide (3.0M solution in 2,2,4-trimethylpentane, 3.57 ml) was added thereto. Then, the mixture was stored in a freezer for 4 days. The mixture was poured into ice and water (50 ml), and the resulting emulsion was filtered through celite pad. The organic layer was separated, washed with brine, dried over magnesium sulfate, and evaporated in vacuo. The residue was purified by column chromatography on silica gel to give (+)-5,5-diphenyl-2-cyclopenten-1-ol (1.84 g, $[\alpha]_D^{21.2}$=+100.8°, C=1.19, CH$_3$OH) and (−)-rel-(1R,2R,3S)-2,3-epoxy-5,5-diphenylcyclopentan-1-ol* [(−) isomer rich mixture] (1.27 g, $[\alpha]_D^{22.4}$=−150.5°, C=0.6276, CH$_2$Cl$_2$).

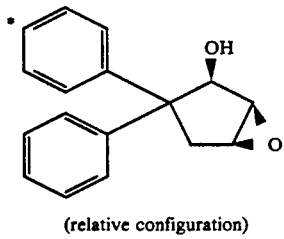

(relative configuration)

Preparation 21

(+)-rel-(1R,2R,3S)-2,3-epoxy-5,5-diphenylcyclopentan-1-ol [(+) isomer rich mixture; $[\alpha]_D^{22} = +45.34°$ (C=0.743, CH$_3$OH)] (−)-5,5-diphenyl-2-cyclopenten-1-ol were obtained according to a similar manner to that of Preparation 20.

Preparation 22

The crude product (−)-rel-(1R,2R,3S)-2,3-epoxy-5,5-diphenylcyclopentan-1-ol [(−) isomer rich mixture], was purified as follows:

The crude product (1.21 g) was recrystallized from ethyl acetate (3 ml) to give its racemate (0.48 g, mp 140°–141° C.). The filtrate was condensed under reduced pressure, and the residue was crystallized from diisopropyl ether (7 ml) to give pure (−)-isomer (0.52 g).

mp: 92.5°–94° C.
$[\alpha]_D^{21.2} = -298.6°$ (C=0.66, CH$_2$Cl$_2$)
IR (Nujol): 3420 cm$^{-1}$
NMR (CDCl$_3$, δ): 1.61 (1H, d, J=12.3 Hz), 2.42 (1H, d, J=15.1 Hz), 3.47 (1H, d, J=15.1 Hz), 3.66 (2H, pseudo s), 4.96 (1H, d, J=12.3 Hz), 7.07–7.35 (10H, m)

Preparation 23

The crude product, (+)-rel-(1R,2R,3S)-2,3-epoxy-5,5-diphenylcyclopentan-1-ol was purified according to a similar manner to that of Preparation 22.

mp: 92°–93° C.
$[\alpha]_D^{22} = +268.17°$ (C=0.465, CH$_2$Cl$_2$)
IR (Nujol): 3450, 3420, 770, 750, 700 cm$^{-1}$
NMR (CDCl$_3$, δ): 1.61 (1H, d, J=12.3 Hz), 2.42 (1H, d, J=15.1 Hz), 3.47 (1H, d, J=15.1 Hz), 3.66 (2H, pseudo s), 4.96 (1H, d, J=12.3 Hz), 7.07–7.35 (10H, m)

Preparation 24

(−)-rel-(1R,2R,3S)-2,3-epoxy-5,5-diphenylcyclopentan-1-ol [(−) isomer rich mixture] obtained in Preparation 20 was recrystallized from ethyl acetate to give (±)-rel-(1R,2R,3S)-2,3-epoxy-5,5-diphenylcyclopentan-1-ol (racemic mixture).

mp: 136°–137° C.
IR (Nujol): 3420, 3050, 800, 770, 750, 740, 700 cm$^{-1}$

EXAMPLE 64

To a solution of (−)-rel-(1R,2R,3S)-2,3-epoxy-5,5-diphenylcyclopentan-1-ol (297 mg) in methylene chloride (3 ml) and isopropyl alcohol (1.2 ml) was added titanium(IV) isopropoxide (0.46 ml) with ice bath cooling. After being stirred for 30 minutes, t-butylamine (0.25 ml) was added thereto, and the mixture was stirred at room temperature overnight. The solution was evaporated in vacuo and the residue was dissolved in diethyl ether (3 ml). To the solution was added 3N hydrochloric acid (1.66 ml) in an ice bath, and the mixture was stirred for 3 hours. The resulting precipitates were collected by filtration, washed with diethyl ether (3 ml), and dried to give (−)-rel-(1R,2S,3R)-3-t-butylamino-5,5-diphenylcyclopentane-1,2-diol hydrochloride (0.36 g).

mp: 279°–281° C. (dec.)
$[\alpha]_D^{19.2} = -77.1°$ (C=0.31, MeOH)
IR (Nujol): 3420, 3350, 3160 cm$^{-1}$
NMR (DMSO-d$_6$, δ): 1.36 (9H, s), 2.63 (1H, dd, J=14.0 Hz and 7.7 Hz), 3.12 (1H, dd, J=14.0 Hz and 9.9 Hz), 3.48–3.72 (1H, br s), 4.09–4.26 (1H, m), 4.68–4.84 (1H, m), 5.15 (1H, d, J=5.8 Hz), 5.23 (1H, d, J=4.9 Hz), 7.00–7.50 (10H, m), 8.78 (1H, br s), 9.17 (1H, br s)

The following compounds (Examples 65 to 68) were obtained according to a similar manner to that of Example 64.

EXAMPLE 65

(+)-rel-(1R,2S,3R)-3-t-butylamino-5,5-diphenylcyclopentane-1,2-diol hydrochloride
$[\alpha]_D^{21} = +74.6°$ (C=0.335, MeOH)
mp: 288° C.
IR (Nujol): 3520, 3320, 1590, 770, 740, 700 cm$^{-1}$
NMR (DMSO-d$_6$, δ): 1.35 (9H, s), 2.52–2.70 (1H, m), 3.01–3.21 (1H, m), 3.50–3.72 (1H, m), 4.08–4.21 (1H, m), 4.77 (1H, t, J=4.8 Hz), 5.15 (1H, d, J=5.8 Hz), 5.21 (1H, d, J=4.8 Hz), 7.00–7.52 (10H, m), 8.71 (1H, broad s), 9.05 (1H, broad s)

EXAMPLE 66

(±)-rel-(1R,2S,3R)-3-t-butylamino-5,5-diphenylcyclopentane-1,2-diol hydrochloride
mp: 278°–279° C. (dec.)
IR (Nujol): 3500, 3300, 3190, 1580, 770, 740, 700 cm$^{-1}$
NMR (DMSO-d$_6$, δ): 1.36 (9H, s), 2.63 (1H, dd, J=14.0 Hz and 7.7 Hz), 3.12 (1H, dd, J=14.0 Hz and 9.9 Hz), 3.61 (1H, broad s), 4.10–4.20 (1H, m), 4.70–4.80 (1H, m), 5.15 (1H, d, J=5.8 Hz), 5.23 (1H, d, J=4.9 Hz), 7.00–7.50 (10H, m), 8.78 (1H, broad s), 9.17 (1H, broad s)

EXAMPLE 67

(±)-rel-(1R,2S,3R)-3-isopropylamino-5,5-diphenylcyclopentane-1,2-diol hydrochloride
mp: 283°–285° C. (dec.)
IR (Nujol): 3500, 3300, 770, 750, 700 cm$^{-1}$
NMR (DMSO-d$_6$, δ): 1.28 (6H, d, J=5.1 Hz), 2.35 (1H, dd, J=13.6 Hz and 9.0 Hz), 3.06 (1H, dd, J=13.6 Hz and 9.0 Hz), 3.25–3.65 (2H, m), 4.15–4.30 (1H, m), 4.71 (1H, pseudo t, J=5.7 Hz), 5.09 (1H, d, J=6.3 Hz), 5.16 (1H, d, J=4.8 Hz), 7.02–7.58 (10H, m), 9.06 (2H, broad s)

EXAMPLE 68

(±)-rel-(1R,2S,3R)-3-diethylamino-5,5-diphenylcyclopentane-1,2-diol hydrochloride
mp: 243°–245° C. (dec.)
IR (Nujol): 3470, 3150, 800, 760, 750, 720, 710, 700 cm$^{-1}$
NMR (DMSO-d$_6$, δ): 1.08–1.35 (6H, m), 2.38 (1H, dd, J=13.2 Hz and 10.0 Hz), 2.94–3.10 (5H, m), 3.42–3.65 (1H, m), 4.28–4.42 (1H, m), 4.67 (1H, dd, J=6.7 Hz and 5.8 Hz), 5.18 (1H, d, J=6.7 Hz), 5.26 (1H, d, J=4.8 Hz), 7.02–7.50 (10H, m), 10.56 (1H, broad s)

EXAMPLE 69

To a suspension of (−)-rel-(1R,2S,3R)-3-t-butylamino-5,5-diphenylcyclopentane-1,2-diol hydrochloride (299 mg) and p-toluenesulfonic acid monohydrate (16 mg) in methylene chloride (6 ml) was added trimethyl orthoformate (0.45 ml), and the mixture was stirred at room temperature overnight. The solvent was removed off by evaporation.

The residue was dissolved in xylene (9 ml), and refluxed for 3 hours. After being cooled, 2.5N sodium hydroxide solution (1.0 ml) was added thereto, and the mixture was stirred for 1 hour. The organic layer was separated and the aqueous layer was extracted with ethyl acetate. The combined organic layer was evaporated in vacuo. The residue was purified by column chromatography on silica gel with a mixture of chloroform and methanol as an eluent to give (−)-N-t-butyl-4,4-diphenyl-2-cyclopentenylamine (130 mg).

This amine was suspended in a mixture of isopropyl alcohol (0.4 ml) and water (0.2 ml). To the suspension was added conc. hydrochloric acid (0.065 ml) in an ice bath, and the mixture was stirred for 5 hours. The resulting precipitates were collected by filtration, washed with 30% aqueous isopropyl alcohol (0.4 ml), and dried to give (−)-N-t-butyl-4,4-diphenyl-2-cyclopentenylamine hydrochloride (89 mg).

The physical data of this compound were identified with those of the compound of Example 10.

EXAMPLE 70

(+)-N-t-butyl-4,4-diphenyl-2-cyclopentenylamine hydrochloride was obtained according to a similar manner to that of Example 69.

mp: 259°–260° C. (dec.)

$[\alpha]_D^{23} = +189.16°$ (C=0.60, MeOH)

IR (Nujol): 3400, 2750, 2700, 1600, 780, 770, 700 cm$^{-1}$

NMR (DMSO-d$_6$, δ): 1.36 (9H, s), 2.34–2.47 (1H, m), 3.33–3.46 (1H, m), 4.44–4.61 (1H, m), 6.03 (1H, broad d, J=5.6 Hz), 6.76 (1H, broad d, J=5.6 Hz), 7.15–7.25 (10H, m), 8.50–8.68 (1H, m), 8.90–9.15 (1H, m)

What we claim is:

1. (−)-N-t-butyl-4,4-diphenyl-2-cyclopentenylamine or its hydrochloride.

* * * * *